United States Patent
Polle et al.

(10) Patent No.: US 9,090,880 B2
(45) Date of Patent: Jul. 28, 2015

(54) REGULATING THE PRODUCTION OF LONG CHAIN HYDROCARBONS

(75) Inventors: Juergen Polle, Brooklyn, NY (US); Duc Tran, Brooklyn, NY (US)

(73) Assignee: Research Foundation of the City University of New York, New York, NY (US)

( * ) Notice: Subject to any disclaimer, the term of this patent is extended or adjusted under 35 U.S.C. 154(b) by 96 days.

(21) Appl. No.: 12/991,020

(22) PCT Filed: Jun. 24, 2009

(86) PCT No.: PCT/US2009/048518
§ 371 (c)(1),
(2), (4) Date: Jan. 20, 2011

(87) PCT Pub. No.: WO2009/158433
PCT Pub. Date: Dec. 30, 2009

(65) Prior Publication Data
US 2011/0104806 A1     May 5, 2011

Related U.S. Application Data

(60) Provisional application No. 61/133,130, filed on Jun. 25, 2008.

(51) Int. Cl.
| | | |
|---|---|---|
| C12P 1/00 | (2006.01) | |
| C12P 5/00 | (2006.01) | |
| C12P 9/00 | (2006.01) | |
| C12P 19/34 | (2006.01) | |
| C12N 9/10 | (2006.01) | |

(52) U.S. Cl.
CPC .................... *C12N 9/1029* (2013.01)

(58) Field of Classification Search
CPC ............ C12N 9/00; C12N 9/10; C12N 13/00; C12N 15/00; C12N 15/09; C12N 15/10; C12N 15/1096; C12N 15/63; C12N 15/64; C12N 15/66; C12N 15/67; C12N 15/68; C12N 15/69; C12N 15/74; C12N 15/79; C12N 15/80; C12N 15/82; C12N 15/87; C12N 2270/32762
See application file for complete search history.

(56) References Cited

U.S. PATENT DOCUMENTS 6,027,900 A * 2/2000 Allnutt et al. ................ 435/6.15

OTHER PUBLICATIONS

Merchant et al., teaching UniProtKB/TrEMBL Direct Submission A8IWL_CHLRE (Dec. 4, 2007) at [http://www.uniprot.org/uniprot/A8IWL1.txt?version=5].*

(Continued)

*Primary Examiner* — Ja'na Hines
(74) *Attorney, Agent, or Firm* — Hoffmann & Baron, LLP

(57) ABSTRACT

The invention relates to isolated polypeptides that include amino acid sequences within botryococcene synthase from different algal species. In another aspect, the invention relates to a method for increasing the production level of a botryococcene hydrocarbon molecule in a cell. The method includes increasing expression of a polynucleotide sequence that encodes botryococcene synthase in the cell. In a further aspect, the invention relates to an algal cell having a polynucleotide sequence that is genetically engineered to express a higher level of botryococcene synthase than a corresponding wild type algal cell, wherein the cell produces an increased level of a botryococcene hydrocarbon molecule than a corresponding wild type algal cell.

7 Claims, 24 Drawing Sheets

GAGAGCGTGGTGGGGCAAATCCGCTTCCAGTGGTGGCGCGACGCGGTGCGGGCG
GCCTACGAGGACCGGCCGCCCAACCACCCCGTGGCCATCGCCCTGGCACACGTG
CTGCACAGCCCCGGGCCCACGCCGCCGCCCGCCCCGGCTCGCATCATCGACGTGC
GTGAATCGGACTTCCTGGACCCGCAGCCGCCGCTGGACATGGGCGCGCTGGAGA
GCTACGCGGAGGGCACCGCCTCGCAGCTGCTGTACCTGCAGCTGGCGGCTGCGG
GCATCAAGCACCGCGACGCCGACCACGCCGCCTCGCACCTGGGTCGGGCCGTAG
GCATCACCACGCTGCTGCGCGGCATGCCGGTGCACGCGGCGGCGCGGCGCAGCT
ACCTGCCCGTGGACCTGTGCGCGGAGGCGCGCGTGTCGCAGGAGGACGTGTACA
GCGGCGTAGTGAGCGAGGGGCTGCGGGACGTGGCGCACAAGGTGGCCAGCCTGG
CCAAGGGCCATCTGGACGAGGCCCGCCGCCTGGCGCCTCGGCTGCCCCGGGCG
CGGCGGGACTCATGCTGCCTGCCGTGGCGGTGGACAGGTACCTG (SEQ ID NO: 1)

ESVVGQIRFQWWRDAVRAAYEDRPPNHPVAIALAHVLHSPGPTPPPAPARIIDVRESD
FLDPQPPLDMGALESYAEGTASQLLYLQLAAAGIKHRDADHAASHLGRAVGITTLLR
GMPVHAAARRSYLPVDLCAEARVSQEDVYSGVVSEGLRDVAHKVASLAKGHLDEA
RRLAPRLPPGAAGLMLPAVAVDRYL (SEQ ID NO: 2)

(56) References Cited

OTHER PUBLICATIONS

Banerjee et al., (Critical Rev. in Biotechnol. 2002. vol. 22(3): 245-279).*
Okada et al., (Archives of Biochem. and Biophysics. 2004. vol. 422:110-118).*
Kucho et al., (Plant Physiol. 1999. vol. 121(4):1329-1337).*
Merchant et al., (UniProtKB/TrEMBLDirect Submission A8IWL_CHLRE (Dec. 4, 2007) at [http://www.uniprot.org/uniprot/A81W-L1.txt?version=5]).*
Palenik et al., PNAS. May 1, 2007. vol. 104(18): 7705-7710.*
A8IWL1_CHLRE: UniProtKB/TrEMBL Submission. [Retrieved from the Internet on Jan. 20, 2011: <http://www.uniprot.org/uniprot/A8IWL1.txt] p. 1-2, sequence.

* cited by examiner

Fig. 1

GAGAGCGTGGTGGGGCAAATCCGCTTCCAGTGGTGGCGCGACGCGGTGCGGGCG
GCCTACGAGGACCGGCCGCCCAACCACCCCGTGGCCATCGCCCTGGCACACGTG
CTGCACAGCCCCGGGCCCACGCCGCCGCCCGCCCCGGCTCGCATCATCGACGTGC
GTGAATCGGACTTCCTGGACCCGCAGCCGCCGCTGGACATGGGCGCGCTGGAGA
GCTACGCGGAGGGCACCGCCTCGCAGCTGCTGTACCTGCAGCTGGCGGCTGCGG
GCATCAAGCACCGCGACGCCGACCACGCCGCCTCGCACCTGGGTCGGGCCGTAG
GCATCACCACGCTGCTGCGCGGCATGCCGGTGCACGCGGCGGCGCGGCGCAGCT
ACCTGCCCGTGGACCTGTGCGCGGAGGCGCGCGTGTCGCAGGAGGACGTGTACA
GCGGCGTAGTGAGCGAGGGGCTGCGGGACGTGGCGCACAAGGTGGCCAGCCTGG
CCAAGGGCCATCTGGACGAGGCCCGCCGCCTGGCGCCTCGGCTGCCCCCGGGCG
CGGCGGGACTCATGCTGCCTGCCGTGGCGGTGGACAGGTACCTG (SEQ ID NO: 1)

ESVVGQIRFQWWRDAVRAAYEDRPPNHPVAIALAHVLHSPGPTPPPAPARIIDVRESD
FLDPQPPLDMGALESYAEGTASQLLYLQLAAAGIKHRDADHAASHLGRAVGITTLLR
GMPVHAAARRSYLPVDLCAEARVSQEDVYSGVVSEGLRDVAHKVASLAKGHLDEA
RRLAPRLPPGAAGLMLPAVAVDRYL (SEQ ID NO: 2)

Fig. 2

ATGATACATGGGCTCTCCAGCGGGCTGCCGAAGGCACGCGTTCTGTGGGGTCACT
TTGGACAGCAGCGGGCGAGCAACGCCATTGCTCGCTCATATGCATCCTTACCTGA
GGACTTGAGGTCTGCTTTCGGCTTCTGTGTGCAACAGGTCAGGCAGTATGACTAC
CTGAACTACGTCTGGGTGGCGCAGATGCCAAAGGATCTGCGGCCTTCGCTGTTCG
CGTTGCGCGCCTTCAACATCGAGACGGCTCTGGTGGCGGACAGCGTCCGCAGCA
AGGAGTCGGTGGTGGGCCAGATCCGCTTCCAGTGGTGGCGAGACGCGGTCAAAG
CCGCCTTCGAAAACCGGCCGCCGAACCATCCGGTGGCGTTTGGAGGCGCTGCTG
GAAACAGCCCGTCACGCTTCAGCCGTTACTGCTTTAAGCGCATCATTGACTGCCG
TGAGGCGGATTTCTTGGACCCACAGCCGCCGCTGGACCTTCAGGCGCTCGAGCAG
TACGCGGAGGGAACGTCGTCTCAGCTCATGTACTTGCAGCTGGCGGCTGCCGGTG
TGAAGCACCAGGACGCGGATCATGCAGCATCGCACCTAGGTCGCGCAGCGGGTA
TCACCACGCTCTTGCGCGGCACAGCCGCCCACGCCGCGGCACGGCGCTGCTACCT
GCCCGTTGACTTGTGCGCGGAGGCGCGCGTTTCGCAGGAGGATGTGTACAGCGG
CGTGGTTTCGGAGGGACTGCGTGATGTCGTACACAAAGTCGCCAGCTTGGCCAA
GGGGCATCTGGACGAGGCGCGACGACTGGCGCCGCGGCTGCCGCCAGGCGCTGC
TGGGGTGATGCTGCCGGCGGTGGCAGTGGGGCGATACTTGGAGGGGCTGGAGGC
TGTGAACTTCAACCCATATGAGACGAAACTC (SEQ ID NO: 3)

MIHGLSSGLPKARVLWGHFGQQRASNAIARSYASLPEDLRSAFGFCVQQVRQYDYL
NYVWVAQMPKDLRPSLFALRAFNIETALVADSVRSKESVVGQIRFQWWRDAVKAA
FENRPPNHPVAFGGAAGNSPSRFSRYCFKRIIDCREADFLDPQPPLDLQALEQYAEGT
SSQLMYLQLAAAGVKHQDADHAASHLGRAAGITTLLRGTAAHAAARRCYLPVDLC
AEARVSQEDVYSGVVSEGLRDVVHKVASLAKGHLDEARRLAPRLPPGAAGVMLPA
VAVGRYLEGLEAVNFNPYETKL (SEQ ID NO: 4)

Fig. 3

ATGCTGGCCCGGCGCTGCCTGGCAGCCACCGCAAACGGCAGCCAGCATTTGCAG
TGTGCAGCAGGGCTGTCCCAATTGAGCAGCAGCGCCTATGGCGTTGCCGGCGGC
GGCGCCGCTTCTGCCGCCGTGGGCGGCGGCCGCTGCTACGCCGGCAGCGCTGGG
AGTGGCGGCGAGGCACCGGCCGACATCCGCAAGGCCTTTGCCTACTGCGTGGAG
CAGGTGAAGAAGCACGACTACGAAAACTACCTCTGGGTCACCCAGCTGCCCAAG
CCCCTGAGGGCTCCCATCTTTGCGCTGCGGGCGTTAACGTGGAGACAGGCCTGA
TCAGCCAGCAAGCCAAGTCGGAGATGCTGGTGCTCATGCGGTGCCAGCAGTGGT
GGCGCGACGCGGTGAACGACTGCTTCAAGGGGCGGCCCCGGAGCAGCCGGTGG
TGACGGCGCTGGCAGAGGTGCTGCGCGTGGTACCGCTGACGCGGTACCGCCTGC
AGCAGATGGTGAGCACACGAGAGGAGGACCTGCTGGCCCACGCGCAGCCTGCCA
GCCTGGAGGCGGTGGAGCGGTACGCAGAGGGCACCTCGGGCCAGCTGCTGCTGC
TGCAGCTGGAGGCTGCACGCATCGGCGCAGGCAGCGCTGGCGCTGGAGGCGGCA
GCAGCAGCGACGACGGCAGCGGCAGCACGCCTAGTAGCGGCAGCAGCCCTGCAG
GAGGAGGAGGCGGAGCGGCGGCGGCGGCGGAGCATGGGGCGGCGCACCTGGGC
AAGGCGGTGGGCATTGTGGGCCTGCTGCGCGGCACGTATGCGCTGGGCAGCCAG
CGGCGGGTATACCTCCCCGCCGACCTGTGCCAGCGGCACGGCGTGGGGGATGAG
GACGTGCTGGCTGGGCGCGACTCGCCAGGGCTGCGCGACGTGACGCTGGCCGTC
GCCTCCGCCGCCAAGCAGCACCTGGACGACGCGCGGCGGCTGGCGGCTGACGTG
GCGCCAGCCGCGCGGCCCCTCTTTGCGCCCGCCGTGGCGGCCGCCATGTACTTGC
AGGCGCTGGAGCAGGCGGGCTTCAACCTGTTCGACCAGCGCATGCTGCGGGGGG
CCTTCTCCCCGCTGGCCTACCAGCTGCGCCTCAAGTGGGCGCTGCTGCGCAACAG
CTACTGA (SEQ ID NO: 5)

MLARRCLAATANGSQHLQCAAGLSQLSSSAYGVAGGGAASAAVGGGRCYAGSAGS
GGEAPADIRKAFAYCVEQVKKHDYENYLWVTQLPKPLRAPIFALRAFNVETGLISQQ
AKSEMLVLMRCQQWWRDAVNDCFKGRPPEQPVVTALAEVLRVVPLTRYRLQQMV
STREEDLLAHAQPASLEAVERYAEGTSGQLLLLQLEAARIGAGSAGAGGGSSSDDGS
GSTPSSGSSPAGGGGGAAAAAEHGAAHLGKAVGIVGLLRGTYALGSQRRVYLPADL
CQRHGVGDEDVLAGRDSPGLRDVTLAVASAAKQHLDDARRLAADVAPAARPLFAP
AVAAAMYLQALEQAGFNLFDQRMLRGAFSPLAYQLRLKWALLRNSY (SEQ ID NO: 6)

Fig. 4

ATGGCCCAGCAAAATCTGCGATCTGCTCTGGCGTATTGTGTGAACCAAGTCAGAT
CCTTTGACTACACAAACTACGTCTGGACCATTCAGATGCCAAAGGAGCTGCGAGC
GCCGCTGATAGCGCTGCGAGCCTTCAATGTGGAGCTGACGCAGATCCCTGACAA
CGTGAAGCAGGAGCAGCTGATGCAGATTCGCATGCAGTGGTGGCGGGACGCCGT
CAAGAGCGCCTACACAGACAAGCCGCAGCCCAATCCAGTCATCCAGGCCCTGCA
CGCGGCGGTGGCGTCGGTGCCGCGGACGCAGTCGCACCTGTTGCGCATGGTGAG
CACCCTGGAGGCGGACTACATGCGCGCGCAGCCGCCCCAATCACTGGAGCAGCT
GGAGCAGTATGCAGAGGGCAGCTCCTCCCAGCTGCTCTACCTCCAGGGCAGGGT
TGCAGGGGTGGATGATGAGCACTTTGACCACGCCGCCTCCCACCTCGGCAAAGCT
GTGGGGATCGCCAACCTTTTGCGGGGGACCGCCTACCATGCTGCCAGGAGGCGG
TGCTACCTGCCGAGCGACCTGTGCATGAGTGAGGGAGTCTCAGATGAAGATGTG
CTGCGGGGCCAGAACACCGACAATGTCTCCAACGTTGTTTTCCAAGTAGCCACCC
AGGCCAAGGGCCATTTGGACGAGGCAAGGGCGCTTAGCAAGCAGTTACCGGCAG
AGGCAAAGCCGCTAATGCTGCCAGCTGCGGCAGTGGATTTGTATCTGAAGGCCCT
GGAGAAGCACGAGTTCAATGCCTTTGCGCCGCAGCTGCAGTCCGGCGGGTTCAC
ACCCCTCTGGCACCAGCTTCTGGTCAAGTACAACCTGATGCTTGGCAGATTTTGA
(SEQ ID NO: 7)

MAQQNLRSALAYCVNQVRSFDYTNYVWTIQMPKELRAPLIALRAFNVELTQIPDNV
KQEQLMQIRMQWWRDAVKSAYTDKPQPNPVIQALHAAVASVPRTQSHLLRMVSTL
EADYMRAQPPQSLEQLEQYAEGSSSQLLYLQGRVAGVDDEHFDHAASHLGKAVGIA
NLLRGTAYHAARRRCYLPSDLCMSEGVSDEDVLRGQNTDNVSNVVFQVATQAKGH
LDEARALSKQLPAEAKPLMLPAAAVDLYLKALEKHEFNAFAPQLQSGGFTPLWHQL
LVKYNLMLGRF (SEQ ID NO: 8)

Fig. 5

ATGACGCTCGCGTTGGACGCGTGCGGGATCAGGAACACGGACGCGGATCACGCG
GCCAGTCATCTCGGGAAGGCGATTGGATTGAGTGCATTACTGCGCGGGACGACG
GCGCACTCGCGTCAGAGGCGATGTTACCTTCCGATTGACGTCTGCGCGCGCCACG
GCGTGAGCACGGAGAGCGTCTATCGCATGGAACCGAGCGAGGGCGTGCGAAGCG
CGGCGCACGAGGTGGCGTGCGCGGCGAAGGCGCACTTAGACAGCGCTCGCGCGA
TGACGGAACGAGTTCCGAAGGAGGCCAAGCCGTTCTTCTTACAAGCGGTGACGG
TTGGACGGTACCTAGACGCGCTCGAGGCGCGAGACTTTGACGTCTTCGACGAAA
CCGTCGCCAAGGGCGGCGCGCCGCTCGCGACTCAGGGCGCGATCGCGTGGCATG
CGTTTCGAGGGACGTATTAG (SEQ ID NO: 9)

MTLALDACGIRNTDADHAASHLGKAIGLSALLRGTTAHSRQRRCYLPIDVCARHGVS
TESVYRMEPSEGVRSAAHEVACAAKAHLDSARAMTERVPKEAKPFFLQAVTVGRYL
DALEARDFDVFDETVAKGGAPLATQGAIAWHAFRGTY (SEQ ID NO: 10)

Fig. 6

TCGACGAGCGCGTCCACGGACGATCTGCGCGCCGCGTTTCGTCACTGCGTCGAAA
TCGTTCGCGCGAGAGACTACGAAACCTATCTCTGCACGCTCGCCCTGCCCCGCGC
GAGCGCGCCCGCGGCGTTCGCCGTGCGCGCGCTGAACGCGGAGACCGGTTCGGT
GGTCGGGAACGCGGAATCCGTCGACGCGGCGGTGGCGCGGTTGATGTGGTGGCG
AGAGACGATGACGGCGGGGAGCGCCGGGACACGGGCGGGTCACCCGGTGGCGC
TCGCAACGCTCGCAGCGCTGGGAAACGAGCCGAACGCGCGCGCGAGAACTTGGA
TGCGACGAATGATTGAGGCGAGGATCGCGGACGCGCGCTCGGATGGACCGCCGC
GGACGATTGCAGATCTAGAGCGGTATGCGAGCGACGCGCACGGGAGCGCGTTGA
CGCTCGCGCTCGACGCGTGCGGAGTCAGGAATGCGGACGCGGATCACGCGGTGA
GTCACTTAGGGCAAGCGATAGGACTAAGTGCGTTATTGCGCGGTACCGTGGCGC
ACGCGAAACAGCGTCGATGTTACTTACCGAGCGACGCGTGCGCGCGGCACGGGG
TGAGCACCGAGAGCGTCTATCGCATGGAGCCGAGCGAGGGCGTGCGTAACGTCG
CGCACGAAGTCGCGAGCGCGGCCAAGGGGCATTTAGATAGCGCGCGCGCGATGG
CGAGCAGAGTTCCCGACGACGCCAAGCCGTTCCTTCTGCAAGCGGTCCCCGTTGG
GAGGTATTTAGACGCGCTCGAGGCGAGAGATTTCGACGTTTTCGACGAAGCCGTC
GCCAAGGGCGGCGCCCCGCTCTTGACGCAAGGCGCCATCGCCTGGCACGCGTTC
AAACGCGCGTAT (SEQ ID NO: 11)

STSASTDDLRAAFRHCVEIVRARDYETYLCTLALPRASAPAAFAVRALNAETGSVVG
NAESVDAAVARLMWWRETMTAGSAGTRAGHPVALATLAALGNEPNARARTWMR
RMIEARIADARSDGPPRTIADLERYASDAHGSALTLALDACGVRNADADHAVSHLG
QAIGLSALLRGTVAHAKQRRCYLPSDACARHGVSTESVYRMEPSEGVRNVAHEVAS
AAKGHLDSARAMASRVPDDAKPFLLQAVPVGRYLDALEARDFDVFDEAVAKGGAP
LLTQGAIAWHAFKRAY (SEQ ID NO: 12)

Fig. 7

ATGCCTTCCTCTGCAAGAGAAGCATTCTTTGCACTACGAGCTTTCAATGTTGAAA
TTGCGAGTATCAAAGATTCATCTATGTTAATGGGTGGAAGATCTCGTGGACGTCG
TGACACTGATGGGGAAGGAGAGGGGATGGGTGACTCCTCGCTGGCTTCTAGATT
ACGAATGCAGTGGTGGCGCGATGGTATAGCGGAAGTGTACGACGATATGGATAC
TACGGATGACCTACAACAGAAACAATCATCACAAGATCCAATCCTTCGTTCATTG
ACCTCTTCACGAAAGCTCAATCCAACGTTGCGGAGTCTGACACAAGCGATTCATA
CTCATCAATTGACGCATCGGTTTCTGAGGAGAATGATGGAAGCAAGAGAAAAAG
ATTTAGAGGTGATGCAGTATGAGAGGTATAGGGATGTCGCTCAGTACGGGGAGG
ATACTGTTTCGAGTGTGTTGTATTTGAGTTTGGAGTGTGTTGGGGTTCGAGACGA
TCAATCGGATTTAGTGGCCTCGGACATCGGTGTTGGTCTAGGACTCATCACTTCG
CTCAGATCTACCGCGTTTCGTGCTACTCAAGGAGAATGCTCCGTTCCTTTTGATCT
TGCAACTAAACACTCTGTTACAATGGATACCATTTGGAGTGCTTGGAATGCATCA
ATAACGATATTGTTACTGAGAACGAAGAATCAAAGTCGGCTCAGGAAGCATTA
CGGGATACAACACGTGAATTGGCGGCGATGGCAGCGTTTCACTTGCATCGTGCAC
GCGAAAATCAAGGCACGGTGCCGAAAGAAGGACGGCCGTGTCTGCTGCCAGCAG
TATGCGGGTTGCAGTATCTGAATGCACTGGAAGCATGCAACTTTGATGTGTTGCA
TCCATCTTTAGTGGGCAGTTCAGAAGGCGATGGTGACGTGGGAGTCGACAGAAG
CAGACGTTTAAACTTGATGCTTCTTCTTGGGAGAGCCTGGTTGACTGGCACCTTTT
GA (SEQ ID NO: 13)

MPSSAREAFFALRAFNVEIASIKDSSMLMGGRSRGRRDTDGEGEGMGDSSLASRLRM
QWWRDGIAEVYDDMDTTDDLQQKQSSQDPILRSLTSSRKLNPTLRSLTQAIHTHQLT
HRFLRRMMEAREKDLEVMQYERYRDVAQYGEDTVSSVLYLSLECVGVRDDQSDLV
ASDIGVGLGLITSLRSTAFRATQGECSVPFDLATKHSVTMDTIWSAWNASNNDIVTE
NEESKSAQEALRDTTRELAAMAAFHLHRARENQGTVPKEGRPCLLPAVCGLQYLNA
LEACNFDVLHPSLVGSSEGDGDVGVDRSRRLNLMLLLGRAWLTGTF (SEQ ID NO:
14)

Fig. 8

```
ATGGGGCGAAAGAAGAAAATTGCATCCCAGCAACCGGAATCATCGAATCAACCG
GCTAAGAAAGCAAAGCCAGAAACTGGTCCGTCGTTTCTCGTGAAAAAGTACCGG
CCGGATAAGCATTATGCATCGATGGACGCTTTCGTCAAGTACGCGAAGTCTCACC
GAATGCTGGACGCGGCCTATGTACAATGGAACAAAGGCGTAACGGCCGAGAAGC
CGTTTGTTTTTTCTGTACGGGTGGGTGGGGTAGACCTCGGTTGGGGGCGGGGGAA
GACGCGTGAGGCTGCCATGGAATGTGCCTGCCGAGCAGCCTTTGCCTTGGTTGGA
GCTCACGGGTATAAAAATTGGACAATTGATGACAACTGCTTGATGGAAGAACCA
GTAGATGTGCCTCCTCCACCACCGCCTCCGATGCCCGGCGCGATGGCGCTCGGCT
TGCCTCCTTACCCTCCAGGCAGCCTCCCTCCTCCTCCCATGCCCGGCTTTTTACCA
CCGCCTCCCCTTCCCGGTATGCTTGCGCCTCCGCTGCCTCCCGGTGCGCCACCGCT
TCCTGATGCACCCCCACCTCCAATGGCAGCGGACCTTATCCCTCAGCCCCAAATG
GTATCGAACCAAGCGCCCGTAGCAACGAGCGTAGCGTCCGGTGTCGCCAATAAT
GTGAACTCTGCTGTAAGTGATGCGTATACAACTTCTGCAAGCGTATCTCTCAATT
TTGGAAAGCCTGCTGTTGTGAAGAGTCAGCGAAAGCAACTCAAGGGTGGATTGA
CTCTTGTGTACGATCCGCTCTCGGAAGGAATGGAAGAACTGAGTATGGAAGAAC
GACGAGCTAGCCTAGAAAGATATCAAAAAATGTTGGTGCGCTCTGTGGCCAAGG
TGGCGAATAGCGGAGAATTTTTTTGGGAATATCAAGAAACGTAAGTTGTTACAT
TGGCAATCTTTTGGTGTCTTGCCGGTAAAGCCCATCATTGGAAGCATTGACTAT
GAGGTAATAAGAACTTTTCTCATGGCTTCACTTCTACTTTCGCTATTGACAGTGAG
CAGACGAGCGAGCTCTATGAGTGTGGCTAAAGGCGCATTGACTCGTCAAGGGCC
TGGCATTTATCTATCGAAGTCGGCGCCAATTCGATGCACGCTTCAACAACAACAA
CAACAATCTCTATCAACCAGAAGCAGCGATGATCAACGAAATCAGAGCGCTGGT
CAAGTTATCAAGGACCACCAATACTGCGTTGATCTTGTCCGCGAGCGGGACAGG
GAAGGATACCGAGCTACCAAAGCGTACTTTGCCATACGGGCCTTTAATGTTGAGC
TAGCGTCCGTCAAAGACTCTCACAACTTGCGCCGTCGGGAGCAGCCTGGCCAAC
AAGAGTCTTCGAGTAGTGTTGCCCTGCAAATGCGCATGCAATGGTGGAGAGACG
CCTTGAAGGAAATTTACGAAGACGAAATGAGTGTTGCTGCTGATCCTATTCTAAG
GAATCTATCGGTGTCCTGCTGGCACAATCCTGTCGTTCGAGCTTTGTCCCAAGCTC
ACCAGCAATGTGACTTGACACGGCGCTTCCTCGAACGCTTGATTGATGCTCGCGA
TTACGACCTCAGTGTTGCGCAGTATTCTTCGATGAATGAAGCGGCAACCTATGCA
GAGGATACCATTTCGAGTCTTCTGTACCTAGCCCTGGAGTGTACAGGGACTCGCG
ACGACAATGCTGATGAAGTCGCTTCATACGCTGGTGTCGGGATAGGTCTAACGAC
AGCCCTACGCGCGACGCCCTTTCGATTAATGCATGGTGAAATACCCATTCCAAAG
GATCTGCTGCGCCCAGCTTTTCCTTACCAGGAATTGATGAAACAGACCGAAGAGG
AATATACGTTGATAGAATCCGACGCGATAGCATTTCGCGAGGCAGTCCGGCACA
TGGCAAATGCTGCTTCCACCAGTTTAGCTCGTGCGCGCGATATTCAGGGGCATGT
ACCGAGGCATGCTAGAGCTTGCTTGCTACCGGTTGTCCCGTCAATTCATTTCCTTT
CAAAGCTGGAGGGCGTCGATTATCACTTGTTTGACCCGAAGCTGAACGATGACA
CACGACTGCGATTAATGTTACTCATGGGACGAACATGGCTCACAGGAATCTTCTA
G (SEQ ID NO: 15)
```

Fig. 8 continued

MGRKKKIASQQPESSNQPAKKAKPETGPSFLVKKYRPDKHYASMDAFVKYAKSHRMLDA
AYVQWNKGVTAEKPFVFSVRVGGVDLGWGRGKTREAAMECACRAAFALVGAHGYKNWT
IDDNCLMEEPVDVPPPPPPPMPGAMALGLPPYPPGSLPPPPMPGFLPPPPLPGMLAPPL
PPGAPPLPDAPPPPMAADLIPQPQMVSNQAPVATSVASGVANNVNSAVSDAYTTSASVSLN
FGKPAVVKSQRKQLKGGLTLVYDPLSEGMEELSMEERRASLERYQKMLVRSVAKVANSGE
FFLGISRNVSCYIGNLFGVLPVKPIIGSIDYEVIRTFLMASLLLSLLTVSRRASSMSVAKGALT
RQGPGIYLSKSAPIRCTLQQQQQQSLSTRSSDDQRNQSAGQVIKDHQYCVDLVRERD
REGYRATKAYFAIRAFNVELASVKDSHNLRRREQPGQQESSSSVALQMRMQWWRD
ALKEIYEDEMSVAADPILRNLSVSCWHNPVVRALSQAHQQCDLTRRFLERLIDARDY
DLSVAQYSSMNEAATYAEDTISSLLYLALECTGTRDDNADEVASYAGVGIGLTTALR
ATPFRLMHGEIPIPKDLLRPAFPYQELMKQTEEEYTLIESDAIAFREAVRHMANAAST
SLARARDIQGHVPRHARACLLPVVPSIHFLSKLEGVDYHLFDPKLNDDTRLRLMLLM
GRTWLTGIF (SEQ ID NO: 16)

Fig. 9

TCCATCTACGCCTGGTGCCGGCGCGCCGACGACGTCGCCGACGAGGTCGGCGTG
AACAAGGGTTTGGCGCTCGCGAGCCTCGACGAGATCGAGGCCGATCTGGCGGCG
GCGCTCCGCGGGAGCCCGCGGAACGCCATCGACGCGGCGCTCGCCGCGACCTTC
GAGGCCTACCCGGCGCTGTCGACGGCGCCCTTCGAGGCCATGCTCGAGGGCATG
CGCGGCGACCTGCGGCCGGAGAGTCTACGGTTCGAGCGCTGGGACCCGGACCTG
AAAACGTACTGCGAGCGCGTCGCGGGCGGCGTGGGGCTCATGCTGCTCCCGCTG
CTCGGCGCGACACCCGACCCCGTCGTGGAGCGGCGGGCCGTGGACCTGGGCGTC
GCCATCCAGCTGACGAACGTGCTGAGAGATGTAGGGGCGGACGCGCGCGACTAC
GACCGGGTCTACCTGCCCCTGGCGGACCTCGCGGCCTGCGGCTGCGACCTGGAG
GACGTGCGGAAGGGGCGGCTGACGGCGCCCTACAAGGACGCCGTGCGGCTGCAG
ATATCGCGCGCGCGCGACCTCTACGCGTCCGCGCGCCTCGCGATCCCGGACCTGC
CCAAGGCGTCGCGGCTGCCCGTGGCGGCCATCGTCGAGCTGCTCGAGAGCATCG
TCGACGAGCTCGAGGCGCGCGACTGCGACTCGCTCTCG (SEQ ID NO: 17)

SIYAWCRRADDVADEVGVNKGLALASLDEIEADLAAALRGSPRNAIDAALAATFEA
YPALSTAPFEAMLEGMRGDLRPESLRFERWDPDLKTYCERVAGGVGLMLLPLLGAT
PDPVVERRAVDLGVAIQLTNVLRDVGADARDYDRVYLPLADLAACGCDLEDVRKG
RLTAPYKDAVRLQISRARDLYASARLAIPDLPKASRLPVAAIVELLESIVDELEARDC
DSLS (SEQ ID NO: 18)

Fig. 10 continued
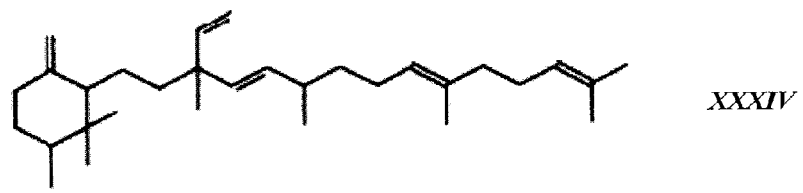
XXXIV
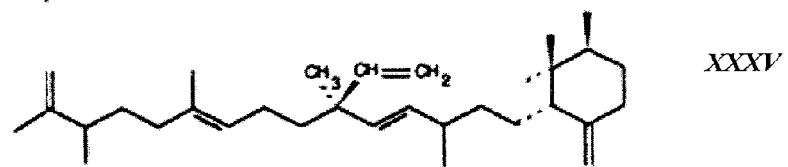
XXXV
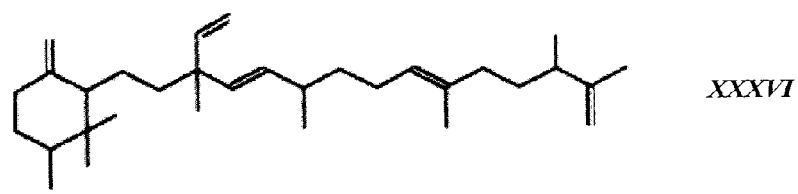
XXXVI
C₄₀H₇₈
(Lycopadiene)
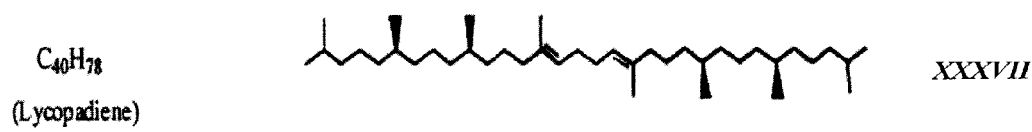
XXXVII
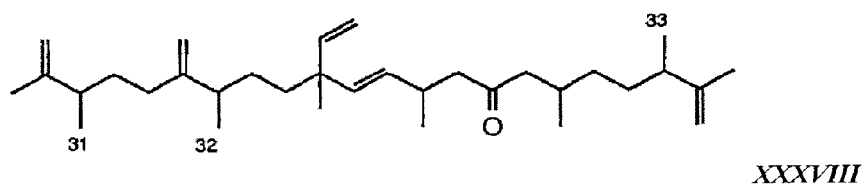
XXXVIII

REGULATING THE PRODUCTION OF LONG CHAIN HYDROCARBONS

CROSS REFERENCE TO RELATED APPLICATIONS

This application asserts priority to an International Application filed under the Patent Cooperation Treaty, PCT/US2009/048518, filed on Jun. 24, 2009, which claims priority to U.S. Patent Application Ser. No. 61/133,130 filed Jun. 25, 2008, the contents of which are incorporated herein by reference.

BACKGROUND OF THE INVENTION

Botryococcenes isolated from algae and other natural sources are useful for generating hydrocarbon precursor molecules that are suitable for biofuels. Botryococcene molecules have been found in crude fossil oils and are therefore valuable for production of oils and other hydrocarbon-based fuels. Extraction of a natural product, such as botryococcenes, from a natural source as photosynthetic organisms is typically limited by the availability of the natural source or the synthetic production of the natural products. Accordingly, there is a need in the art for improved host cells and methods that provide for increased production of botryococcene molecules or an increased production of an enzyme that facilitates in the production of botryococcene molecules.

SUMMARY OF THE INVENTION

In one aspect, the invention relates to an isolated polypeptide that includes an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

In another aspect, the invention relates to a method for increasing the production level of a botryococcene hydrocarbon molecule in a cell. The method includes increasing expression of a polynucleotide sequence that encodes botryococcene synthase in the cell.

In a further aspect, the invention relates to an algal cell that includes a polynucleotide sequence that is genetically engineered to express a higher level of botryococcene synthase than a corresponding wild type algal cell, wherein said cell produces an increased level of a botryococcene hydrocarbon molecule than a corresponding wild type algal cell.

BRIEF DESCRIPTION OF THE DRAWINGS

FIG. 1: cDNA sequence (partial, incomplete at the 5' and 3' ends) coding for and amino acid sequence (partial) of a botryococcene synthase peptide from *Chlamydomonas reinhardtii* algae is provided.

FIG. 2: cDNA sequence coding for and amino acid sequence of a botryococcene synthase peptide from *Volvox carteri* algae is provided.

FIG. 3: cDNA sequence coding for and amino acid sequence of a botryococcene synthase peptide from *Chlorella sp.* NC64A algae is provided.

FIG. 4: cDNA sequence coding for and amino acid sequence of a botryococcene synthase peptide from *Chlorella vulgaris* algae is provided.

FIG. 5: cDNA sequence (incomplete sequence, the 5' end is incomplete) coding for and amino acid sequence (partial) of a botryococcene synthase peptide from *Ostreococcus tauri* algae is provided.

FIG. 6: cDNA sequence (incomplete) coding for and amino acid sequence (partial) of a botryococcene synthase peptide from *Ostreococcus lucimarinus* algae is provided.

FIG. 7: cDNA sequence coding for and amino acid sequence of a botryococcene synthase peptide from *Thalassiosira pseudonana* algae is provided.

FIG. 8: cDNA sequence (5' end needs editing, only the last three exons code for the prenyl transferase) coding for and amino acid sequence (the part of the sequence that does not belong to the prenyltransferase is given in italics) of a botryococcene synthase peptide from *Pheodactylum tricornutum* algae is provided.

FIG. 9: cDNA sequence (needs 5' and 3' editing) coding for and amino acid sequence (the part of the sequence that does not belong to the prenyltransferase is given in italics) of a botryococcene synthase peptide from *Aureococcus anophagefferens* algae is provided.

DETAILED DESCRIPTION OF THE INVENTION

Figure 10:
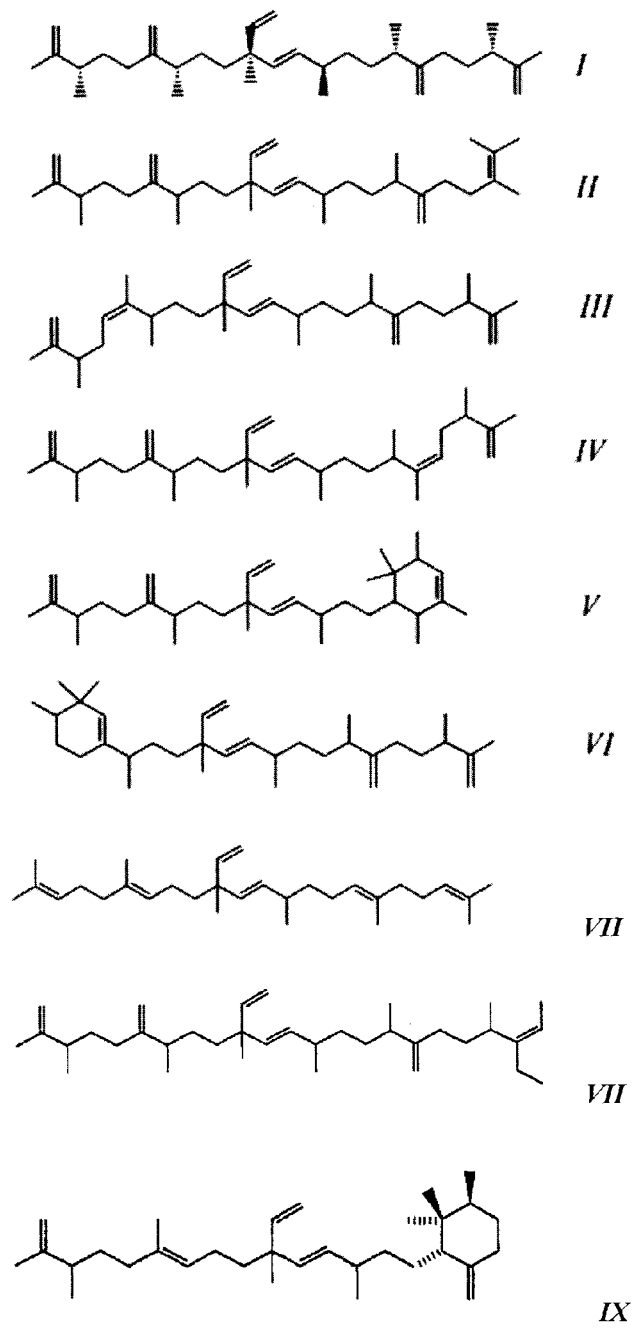
FIG. 10: Exemplary botryococcenes and homologues. Various $C_{34}$ isomeric botryococcenes from *Botryococcus braunii* race B shown in I-VI. $C_{30}$ botryococcene shown in VII, which is the precursor of all higher homologous botryococcene compounds. $C_{36}$ botryococcene homologue (darwinene) shown in VIII. $C_{32}$ botryococcene homologue (braunicene) shown in IX. Various acyclic and cyclic botryococcene hydrocarbon molecules shown in X-XXXVII. $C_{33}$ botryococcene homologue (botryococcenone) shown in XXXVIII.
Figure 10:
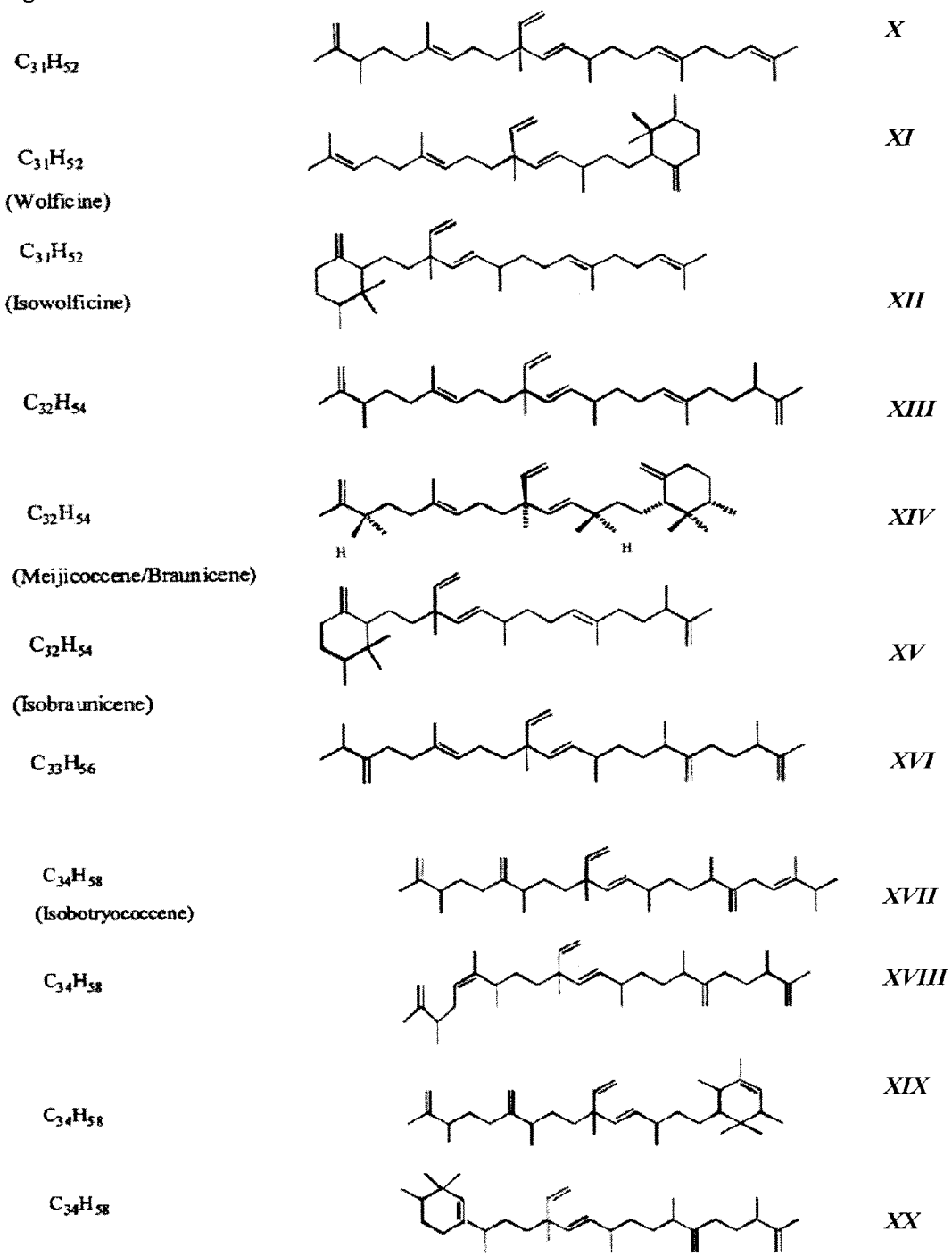
Figure 10:
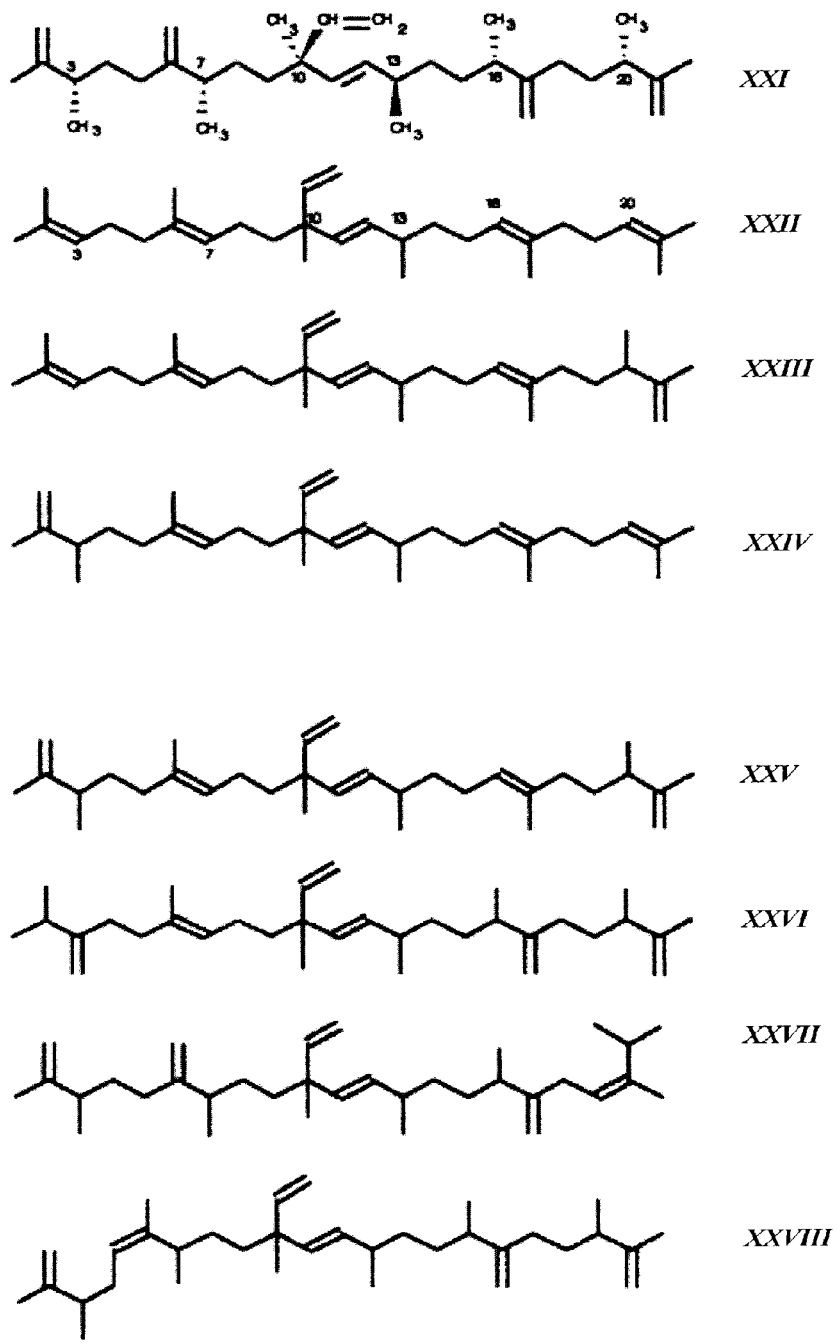
Figure 10:
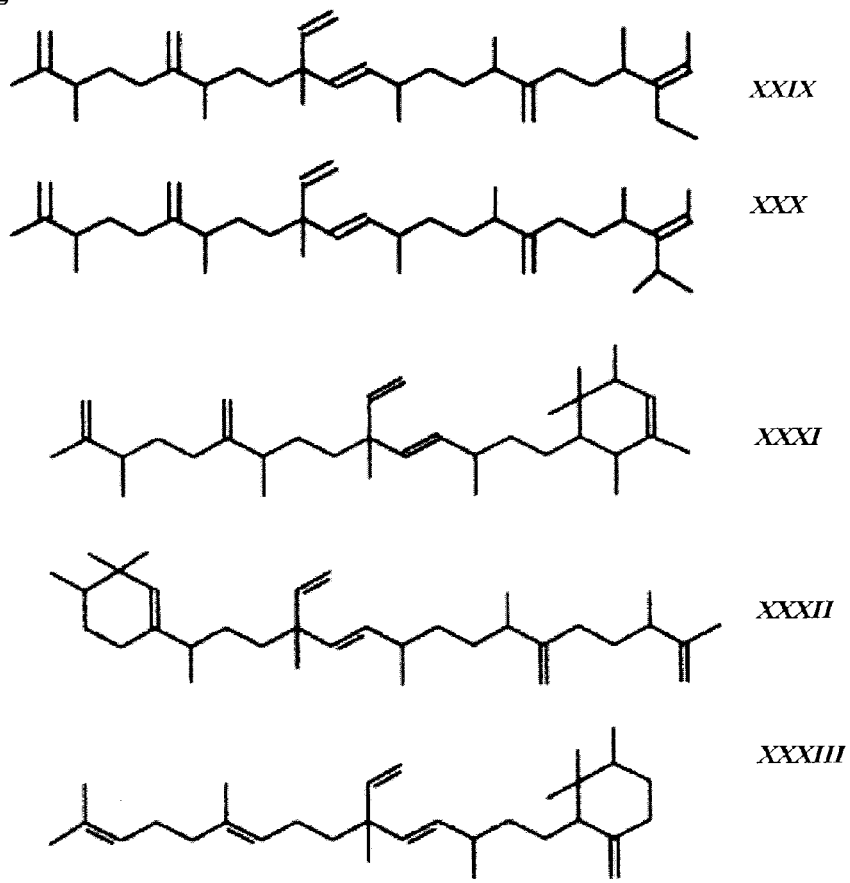
Figure 11:
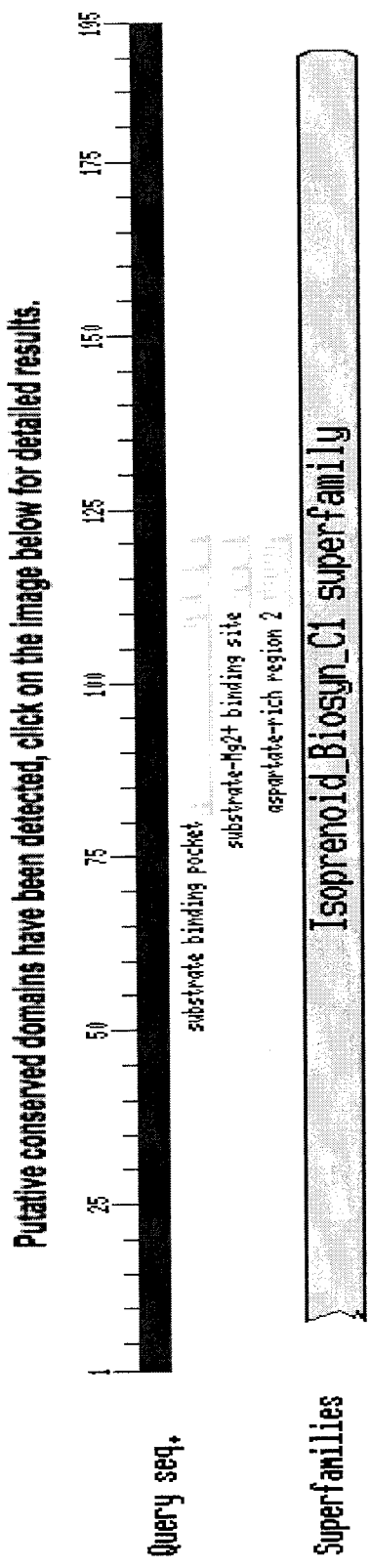
FIG. 11: The result of a Basic Local Alignment Search Tool (BLAST) search in the National Center for Biotechnology Information (NCBI) database performed with the amino acid sequence set forth in SEQ ID NO: 2 is shown.
Figure 12:
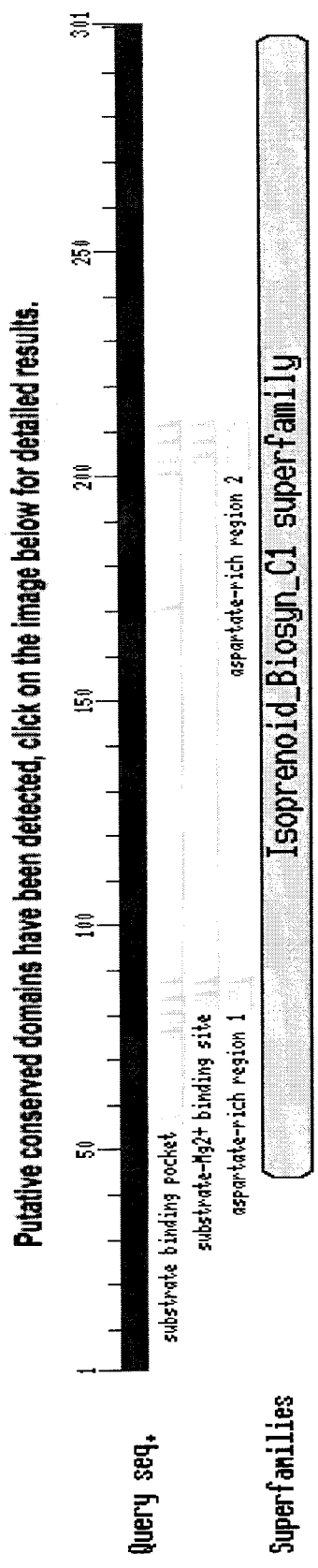
FIG. 12: The result of a BLAST search in the NCBI database performed with the amino acid sequence set forth in SEQ ID NO: 4 is shown.
Figure 13:
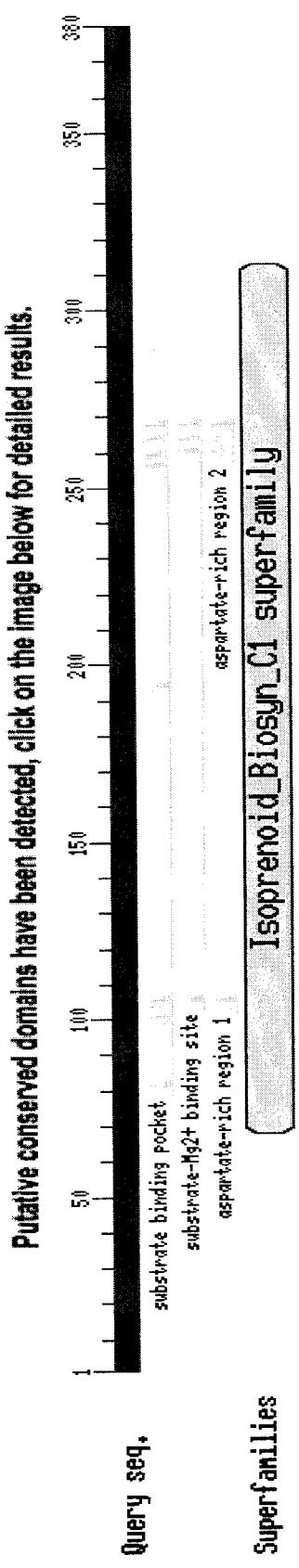
FIG. 13: The result of a BLAST search in the NCBI database performed with the amino acid sequence set forth in SEQ ID NO: 6 is shown.
Figure 14:
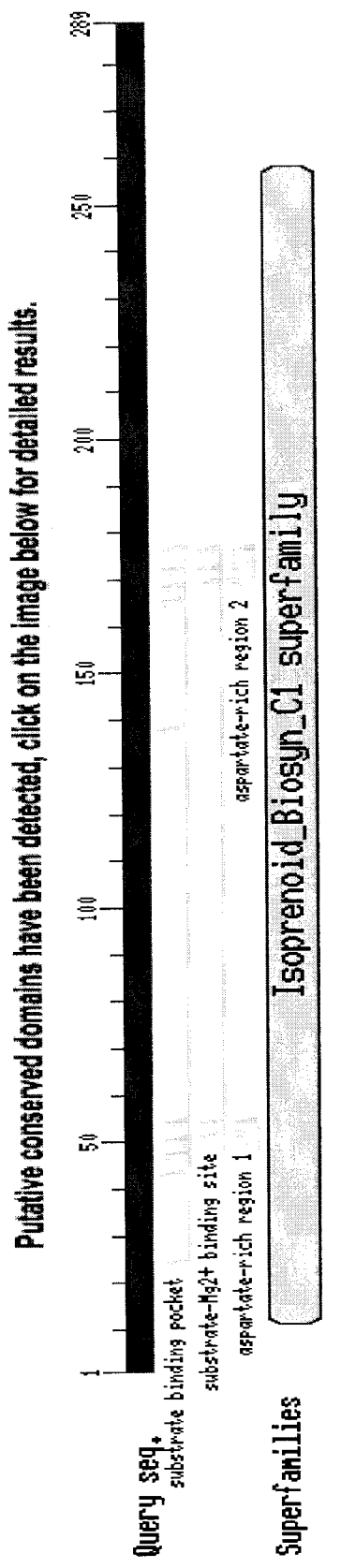
FIG. 14: The result of a BLAST search in the NCBI database performed with the amino acid sequence set forth in SEQ ID NO: 8 is shown.
Figure 15:
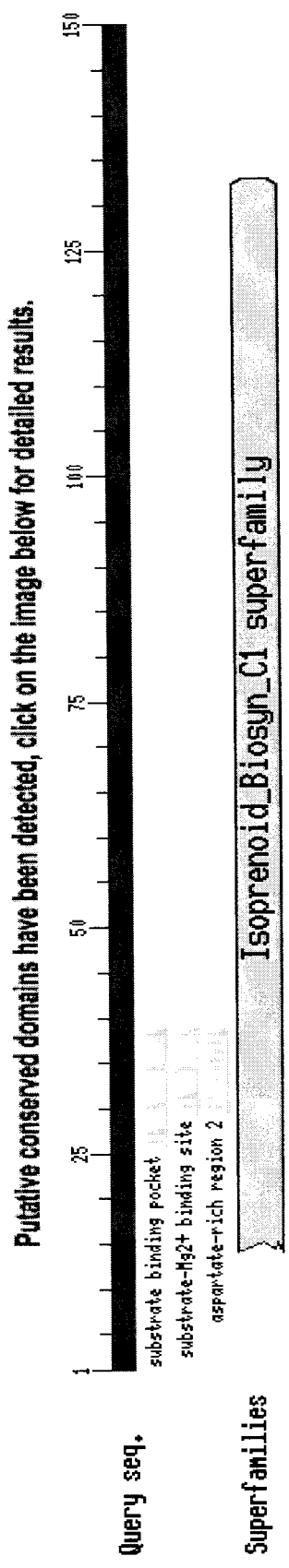
FIG. 15: The result of a BLAST search in the NCBI database performed with the amino acid sequence set forth in SEQ ID NO: 10 is shown.
Figure 16:
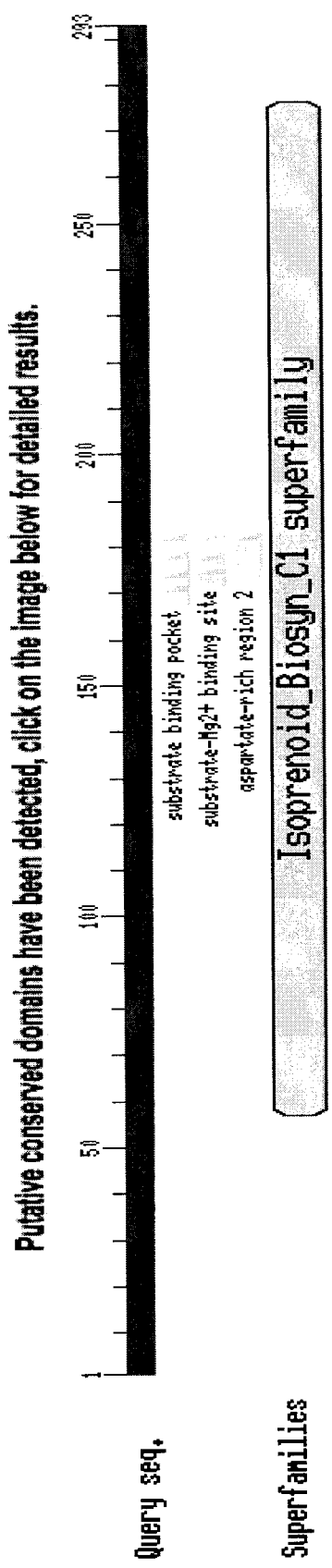
FIG. 16: The result of a BLAST search in the NCBI database performed with the amino acid sequence set forth in SEQ ID NO: 12 is shown.
Figure 17:
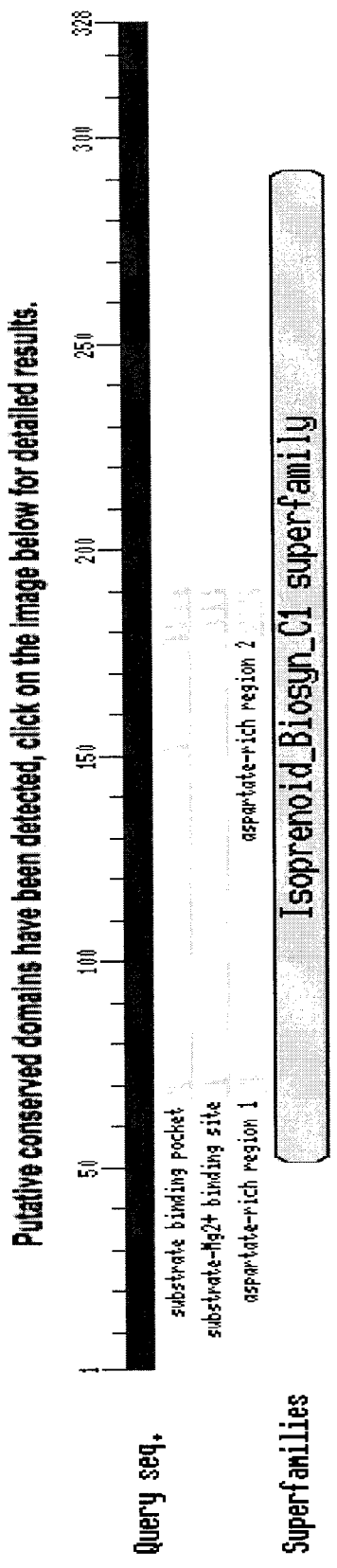
FIG. 17: The result of a BLAST search in the NCBI database performed with the amino acid sequence set forth in SEQ ID NO: 14 is shown.
Figure 18:
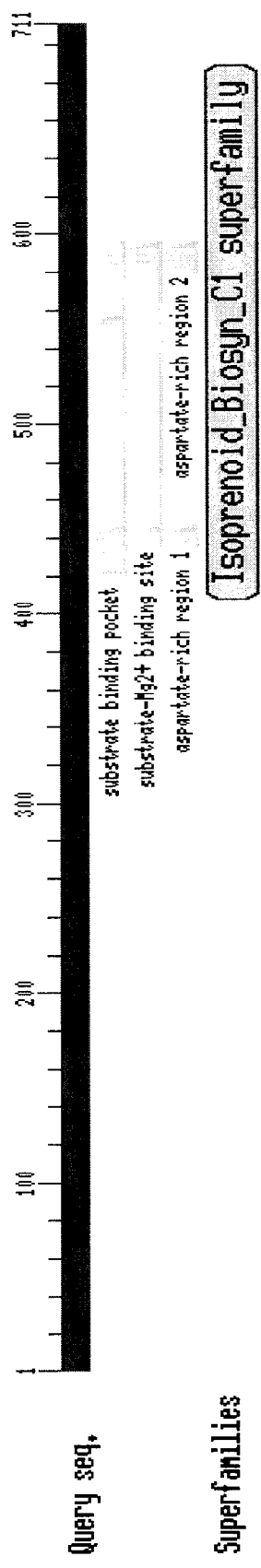
FIG. 18: The result of a BLAST search in the NCBI database performed with the amino acid sequence set forth in SEQ ID NO: 16 is shown.
Figure 19:
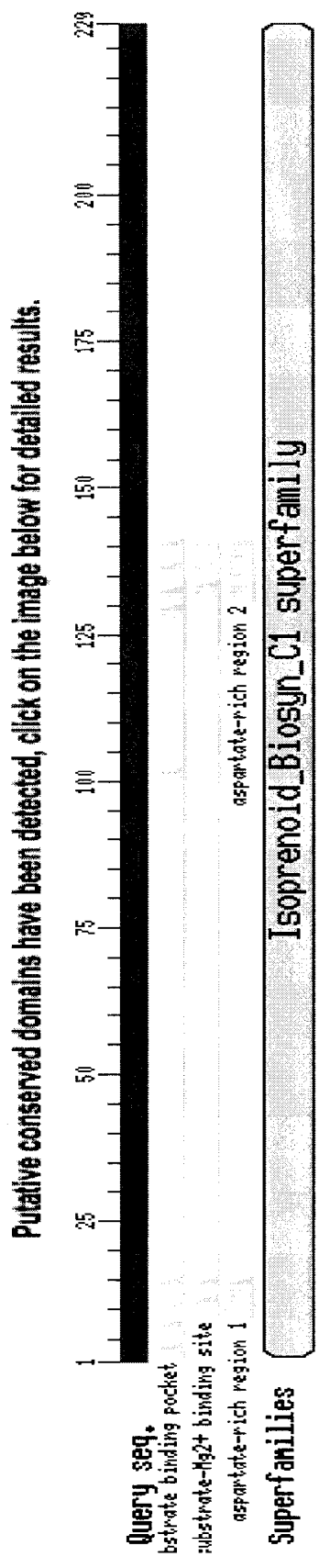
FIG. 19: The result of a BLAST search in the NCBI database performed with the amino acid sequence set forth in SEQ ID NO: 18 is shown.

The inventors have surprisingly discovered novel nucleotide molecules and amino acid molecules that include at least a portion of a botryococcene synthase protein in various species of algal cells. In addition, the inventors discovered that increasing expression of polynucleotide sequences that encode botryococcene synthase increases production of botryococcene hydrocarbon molecules in algae cells.

Isolated Polypeptides

The inventors discovered that botryococcene synthase exists in various algal species. In particular, the inventors identified amino acid sequences within botryococcene synthase from different algal species.

In one aspect, the invention relates to an isolated polypeptide that includes an amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

In one embodiment, the amino acid sequence is at least 90% identical to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, and the polypeptide exhibits a condensation activity. More preferably, the amino acid sequence is at least about 91%, about 92%, about 93%, about 94%, about 95%, about 96%, about 97%, about 98%, about 99%, or about 100% identical to said amino acid sequence, and the polypeptide exhibits a condensation activity. Preferably, the sequence identity is counted over a full length alignment with the amino acid sequence shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18.

By way of illustration, a polypeptide having an amino acid sequence having at least, for example, 95% "identity" to a reference amino acid sequence of SEQ ID NO: 2, is intended that the amino acid sequence of the polypeptide is identical to the reference sequence except that the polypeptide sequence may include up to five amino acid alterations per each 100 amino acids of the reference amino acid sequence of SEQ ID NO: 2.

For example, to obtain a polypeptide having an amino acid sequence at least 95% identical to a reference amino acid sequence, up to 5% of the amino acid residues in the reference sequence may be deleted or preferably substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence, or anywhere between those terminal positions, interspersed either individually among residues in the reference sequence or in one or more continuous groups within the reference sequence.

The polypeptide, however, maintains and exhibits a function of condensation activity. As used herein, the term "condensation activity" refers to an ability of the polypeptide to catalyze a chemical reaction in which two molecules or functional groups combine to form one single molecule, together with the loss of a small molecule. The small molecule lost through the condensation activity may, for example, be water or hydrogen atoms. Preferably, the condensation activity includes head to tail condensation of isoprene units which may be of 5, 10, 15, 20, 30 or 40 carbons in length.

Botryococcene synthase has an enzymatic activity of catalyzing the condensation of two $C_{15}$ molecules of farnesylpyrophosphate (FPP) to a long-chain $C_{30}$ botryococcene hydrocarbon molecule. In addition, botryococcene synthase catalyzes the condensation of two $C_{20}$ geranylgeranyl pyrophosphate molecules to a long-chain $C_{40}$ lycopadiene hydrocarbon molecule. Thus, preferably, the condensation activity of the polypeptides of the invention includes condensation of two $C_{15}$ molecules of farnesylpyrophosphate (FPP) to a long-chain $C_{30}$ botryococcene hydrocarbon molecule and/or condensation of two geranylgeranyl pyrophosphate molecules to a long-chain C40 lycopadiene hydrocarbon molecule.

Preferably, any substitutions of amino acids in the polypeptide are conservative, i.e, within a group of amino acids having similar physicochemical characteristics. Amino acids may be grouped according to their physicochemical characteristics as follows:

(a) Non-polar amino acids: Ala(A) Ser(S) Thr(T) Pro(P) Gly(G);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val(V); and
(e) Aromatic amino acids: Phe(F) Tyr(Y) Trp(W).

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:2374, 1988; Higgins and Sharp, CABIOS 5:151-3, 1989; Corpet et al., Nucl. Acids Res. 16:10881-90, 1988; Pearson and Lipman, Proc. Natl. Acad. Sci. U.S.A. 85:2444, 1988; and Altschul et al., Nature Genet. 6:119-29, 1994.

For example, a mathematical algorithm that can be used for comparing two amino acid sequences or two polynucleotide sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the BLASTN and BLASTX programs (version 2.0) of Altschul, et al. *J. Mol. Biol.* 215:403-10, 1990. BLAST nucleotide searches can be performed with the BLASTN program, score=100, wordlength=12 to obtain nucleotide sequences homologous to the nucleic acid molecules of the invention. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al., Nucleic Acids Res. 25:3389-3402, 1997. When utilizing BLAST and Gapped BLAST programs, the default parameters of the respective programs (e.g., BLASTX and BLASTN) can be used.

The NCBI Basic Local Alignment Search Tool (BLAST™) (Altschul et al., J. Mol. Biol. 215:403-10, 1990) is available from several sources, including the Nation Center for Biotechnology Information NCBI, Bethesda, Md.) and on the Internet, for use in connection with the sequence analysis programs blastp, blastn, blastx, tblastn and tblastx.

A minimum number of amino acids for the polypeptide sequence of the invention is about 200 amino acids, preferably about 225 amino acids, and more preferably about 250 amino acids. Thus, the minimum number of nucleotides in the polynucleotide sequence encoding the polypeptide sequence of the invention is about 600 nucleotides, preferably about 675 nucleotides, and more preferably about 750 nucleotides.

A maximum number of amino acids for the polypeptide sequence of the invention is at most about 325 amino acids, preferably about 350, and more preferably about 400 amino acids. Thus, the maximum number of nucleotides in a polynucleotide sequence encoding the polypeptide of the invention is about 975 nucleotides, preferably about 1050 nucleotides, and more preferably about 1200 nucleotides. Any minimum amount can be combined with any maximum amount to define a range.

In one embodiment, the polypeptide is isolated from *Chlamydomonas reinhardtii, Volvox carteri, Chlorella* sp. NC64A, *Chlorella vulgaris, Ostreococcus tauri, Ostreococ-* cus lucimarinus, Thalassiosira pseudonana, Pheodactylum tricornutum, and Aureococcus anophageferens.

For example, the amino acid sequence set forth in SEQ ID NO: 2 and the polynucleotide sequence in SEQ ID NO: 1 were isolated from Chlamydomonas reinhardtii at the following genomic location: previously known as, Chlre3/scaffold_19: 287440-288937, and now known as Chlre4/chromosome_3:5394038-5395532.

The amino acid sequence set forth in SEQ ID NO: 4 and the polynucleotide sequence in SEQ ID NO: 3 were isolated from Volvox carteri, at the following genomic location: Volcal/scaffold_70: 157557-160115.

The amino acid sequence set forth in SEQ ID NO: 6 and the polynucleotide sequence in SEQ ID NO: 5 were isolated from Chlorella sp. NC64A, at the following genomic location: Ch1NC64A_1/scaffold_25: 455056-456439.

The amino acid sequence set forth in SEQ ID NO: 8 and the polynucleotide sequence in SEQ ID NO: 7 were isolated from Chlorella vulgaris, at the following genomic location: Chlvu1/scaffold_11:218477-221727.

The amino acid sequence set forth in SEQ ID NO: 10 and the polynucleotide sequence in SEQ ID NO: 9 were isolated from Ostreococcus tauri, at the following genomic location: Ostta4/chr_08.0001: 529287-529739.

The amino acid sequence set forth in SEQ ID NO: 12 and the polynucleotide sequence in SEQ ID NO: 11 were isolated from Ostreococcus lucimarinus, at the following genomic location: Ost9901_3/chr_8: 532886-533764.

The amino acid sequence set forth in SEQ ID NO: 14 and the polynucleotide sequence in SEQ ID NO: 13 were isolated from Thalassiosira pseudonana, at the following genomic location: Thaps3/chr12: 289720-290819.

The amino acid sequence set forth in SEQ ID NO: 16 and the polynucleotide sequence in SEQ ID NO: 15 were isolated from Pheodactylum tricornutum, at the following genomic location: Phatr2/chr4: 277875-280738.

The amino acid sequence set forth in SEQ ID NO: 18 and the polynucleotide sequence in SEQ ID NO: 17 were isolated from Aureococcus anophageferens, at the following genomic location: Auran1/scaffold8: 1304824-1305510.

In one embodiment, the polynucleotide sequences that includes SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, encodes a polypeptide that includes an amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, respectively.

The term "polynucleotide sequence" refers to a polymeric form of nucleotides of any length, either ribonucleotides or deoxynucleotides. Polynucleotide sequences may include, for example, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

Method for Increasing Production of Botryococcene Hydrocarbon Molecules

In another aspect, the invention relates to a method for increasing the production level of a botryococcene hydrocarbon molecule in a cell. The method includes increasing expression of a polynucleotide sequence that encodes botryococcene synthase in the cell.

The terms "botryococcene hydrocarbon molecule," "botryococcene molecule," and "botryococcenes" generally refer to a compound that are triterpenoid hydrocarbons having the following formula: $C_nH_{2n-10}$, n=30-37. Such botryococcene molecules are derived form the isoprenoid pathway and have a backbone of two $C_{15}$ farnesyl residues. "Botryococcene hydrocarbon molecule" also includes the tetrapenoid molecule called lycopadiene ($C_{40}H_{78}$), shown in FIG. 10, structure XXXVII, and its derivatives. Examples of botryococcene molecules having various numbers of carbon atoms are shown in FIG. 10, structures I-XXXVII. Botryococcene molecules may be acyclic or cyclic. Preferably, the botryococcene molecule is a $C_{34}$ molecule. More preferably, the botryococcene molecule is a $C_{30}$ molecule.

Botryococcene molecules were first discovered from a wild sample of Botryococcus braunii, race B. The isolated botryococcene molecule from the wild sample was a $C_{34}$ compound, see FIG. 10, structure I. The $C_{30}$ botryococcene shown in VII of FIG. 10 is the precursor of higher homologous botryococcene molecules. The $C_{40}$ lycopadiene molecule was first discovered in a wild sample of Botryococcus braunii, race L, and it is also a precursor of higher homologous botryococcene molecules. Since the species of B. braunii are polyphyletic, the ability to produce botryococcene molecules is not unique to B. braunii. The inventors surprisingly discovered polypeptide sequences isolated from other algal species, which can be used to produce or increase production of a botryococcene hydrocarbon molecule.

Production of a botryococcene hydrocarbon molecule is considered increased according to the invention if the production is increased at least about 10%, preferably, at least about 20%, more preferably at least about 30%, even more preferably at least about 40%, and most preferably at least about 50%, or more, than the production in a corresponding wild type cell. Optimally, production of a botryococcene hydrocarbon molecule is considered increased according to the invention if production is increased at least about 70%, more optimally at least about 85%, and most optimally 100%.

Botryococcene synthase refers to a protein that belongs to a family of prenyl transferases. Accordingly, specific motifs that are characteristic of prenyl transferases are also present in botryococcene synthase, such as, for example, an aspartate-rich region and/or a substrate-$Mg^{2+}$ binding site. See FIGS. 11-19, which shows the approximate locations of aspartate-rich regions and/or substrate-$Mg^{2+}$ binding sites in the respective amino acid sequences. As stated above, botryococcene synthase has an enzymatic activity of catalyzing the condensation of two $C_{15}$ molecules of farnesylpyrophosphate (FPP) to a long-chain $C_{30}$ botryococcene hydrocarbon molecule. In addition, botryococcene synthase catalyzes the condensation of two $C_{20}$ geranylgeranyl pyrophosphate molecules to a long-chain $C_{40}$ lycopadiene hydrocarbon molecule.

The desired polypeptide as used herein includes botryococcene synthase. The desired polypeptide also includes polypeptides that include an amino acid sequence set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, as described above. The polynucleotide sequences that encode these polypeptides include the sequences set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, respectively, as described above. See FIGS. 1-9.

Expression of a polynucleotide that encodes a desired polypeptide can be increased by any genetic engineering means suitable in a cell. The term "genetic engineering" or "genetic engineered" as used herein refers to any recombinant DNA or RNA methods used to manipulate a polynucleotide sequence in a cell to increase the expression level of an encoded protein in comparison to the level of expression of the protein in a corresponding wild type cell. Such genetic engineering methods are described, for example, in Sambrook, J., Fritsch, E. F., Maniatis, T., in: Molecular Cloning (A Laboratory Manual), $2^{nd}$ Edition, Cold Spring Harbor Laboratory Press, 1989.

The genetically engineered cell may include any cell from algae, fungi, bacteria, or higher plants. In one embodiment, the cell is a bacterial cell, preferably an *Escherichia coli* cell. In another preferred embodiment, the cell is an algal cell derived from *Chlamydomonas reinhardtii, Volvox carteri, Chlorella* sp. NC64A, *Chlorella vulgaris, Ostreococcus tauri, Ostreococcus lucimarinus, Thalassiosira pseudonana, Pheodactylum tricornutum,* and *Aureococcus anophagefferens.*

In one embodiment, the polynucleotide sequence that encodes the desired polypeptide is genetically engineered to include additional regulatory sequences operationally linked to the polynucleotide sequence. The term "operationally linked" as used herein refers to linkage of a polynucleotide regulatory sequence to a coding sequence such that the regulatory sequence increases transcription of the polynucleotide coding sequence. A "coding sequence" refers to a polynucleotide sequence that encodes a specific amino acid sequence.

A "regulatory sequence" refers to a polynucleotide sequence that controls some aspect of the expression of another polynucleotide sequence. The regulatory sequence may result, for example, in an increase in the transcription of DNA to RNA, or in an increase in translation from RNA to botryococcene synthase protein. Regulatory sequences include, for example, promoters, enhancers, transcription factor binding sites, polyadenylation signals, termination signals, etc. The term "additional" regulatory sequence refers to a regulatory sequence that is in addition to the number and type of regulatory sequences that are typically associated with the corresponding wild type cell.

The term "promoter" refers to a polynucleotide sequence located upstream or downstream from the start of transcription of the polynucleotide sequence that encodes the desired polypeptide. A promoter drives expression of an operationally linked polynucleotide sequence and is typically located upstream (5') to a coding sequence. A wide variety of promoters useful for an algal cell is known in the art and may be used to enhance expression of the polynucleotide sequence that encodes the desired polypeptide in the algal cell. Examples of suitable promoters include constitutive promoters, inducible promoters, and viral promoters.

The promoter may be derived from the host algal cell, other algal species, or may be obtained from non-algal sources, including bacteria, viruses, yeast, plant, and mammalian cells. The promoter may be constitutive or inducible.

Promoter sequences for an algal cell are preferably isolated from an algal species or a closely related organism. Promoters that are functional in higher plants are less preferred except for groups of algae closely related to higher plants. For example, the 35S CaMV promoter, which is active in many plant species, is completely inactive in *Chlamydomonas* (Day et al. (1990) Physiol. Plantarum 78:254-260).

Specific examples of suitable promoters include hydrogenase promoters, Cytochrome C 6 (Cyc6) promoter, Nia1 promoter, CabII-1 promoter, Ca1 promoter, Ca2 promoter, coprogen oxidase promoter, algal ribulose bisphosphate carboxylase small subunit gene (SSU) promoter, and algal pyruvate kinase promoter. Additional suitable promoters include the arylsulfatase promoter, and the aminoglycoside 3'-phosphotransferase gene (aphVIII) promoter from the multicellular green alga Volvox, atpA promoter, and RbcS2 promoter which has been widely used to drive gene expression in the nucleus of *C. reinhardii*.

Genetic engineering may further include introducing an expression enhancer operationally linked to a polynucleotide sequence that encodes the desired polypeptide sequence, in order to increase expression of the polynucleotide sequence. An "expression enhancer" refers to a sequence of DNA that functions to increase transcription from nearby promoters. An expression enhancer can be either upstream or downstream to the start of transcription. Examples of suitable expression enhancers include enhancer elements, EE-1 (AGATTTTCACCGGTTGGAAGGAGGT)(SEQ ID NO: 36) and EE-2 (CGACTTACGAA) (SEQ ID NO: 37), as described in Kucho et al. (*Plant Physiol.* 2003 October; 133(2):783-93); the GCC-box enhancer element, as described in Wu et al. (*Mol Genet Genomics.* 2001 July; 265(5):763-70); and those described in Fischer, et al. (*Mol Genet Genomics.* 2001 July; 265(5):888-94) regarding flanking regions of PsaD.

In another preferred embodiment, at least one additional polynucleotide sequence, and preferably multiple polynucleotide sequences, that encode the desired polypeptide is functionally introduced into an algal cell. The polynucleotide sequence may, for example, be incorporated in a vector that is then used to functionally introduce the additional polynucleotide sequence into an algal cell.

The introduction of polynucleotide sequences can be either temporary, e.g., by use of vectors, or permanent, e.g., by integration of the entire vector or a fragment thereof into either the nuclear genome, the plastid genome, or the mitochondrial genome of the host alga.

Suitable vectors for increasing expression of the polynucleotide sequence that encodes the desired polypeptide sequence in an algal cell are known in the art, such as the expression vectors described in U.S. Pat. No. 7,232,679. Such vectors for increasing expression of the polynucleotide sequence are incorporated herein by reference. For example, suitable vectors include pBBR-K-mev-op16-1, pBBR-K-mev-op16-2, pDS-mvaA, pDS-idi, pDS-hcs, pDS-mvk, pDS-pmk, pDS-mvd, pDS-His-mvaA, pDS-His-idi, pDS-His-hcs, pDS-His-mvk, pDS-His-pmk, pDS-His-mvd, pBBR-K-Zea4, pBBR-K-Zea4-up, pBBR-K-Zea4-down, pBBR-K-PcrtE-crtE-3, pBBR-tK-PcrtE-mvaA, pBBR-tK-PcrtE-idi, pBBR-tK-PcrtE-hcs, pBBR-tK-PcrtE-mvk, pBBR-tK-PcrtE-pmk, pBBR-tK-PcrtE-mvd, pBBR-K-PcrtE-mvaA-crtE-3, pDS-His-phaA, pBBR-K-PcrtE-crtW, pBBR-K-PcrtE-crtWZ, pBBR-K-PcrtE-crtZW, and combinations thereof.

Methods and vectors for genetically engineering an algal cell are well known in the art. A person having ordinary skill can readily adapt the known methods and vectors for use in enhancing expression of botryococcene synthase or polypeptide sequence that includes SEQ ID NOs: 2, 4, 6, 8, 10, 12, 14, 16, or 18 in algal cells. See, for example, the disclosure in Melis et al., (U.S. patent application Ser. No. 11/770,412, specifically Example 1, column 9, paragraph [0092] of US Publication No. 2008/0038805) regarding methods and vectors relating to genetic modification of microalgae to increase expression of Dxs and Dxr genes; Hallmann et al. (*Proc Natl Acad Sci USA.* 1994 Nov. 22; 91(24):11562-6, specifically page 11563, section "Transformation") regarding methods and vectors relating to genetic modification of *Volvox carteri* alga to increase expression of a pheromone; and Xue et al, (U.S. Pat. No. 7,081,567, specifically Example 1, Section I—"Culture of *Dunaliella salina*," and Section III—"Introducing Foreign Target Genes into the Cells of *Dunaliella salina*") regarding genetic transformation (functional introduction) techniques that include introducing a foreign target gene into the cells of *Dunaliella salina* and screening the transformed cells of *Dunaliella salina*. The general methods and vectors for genetic engineering microalgae disclosed in Melis et al., Hallmann et al., and Xue et al. are incorporated herein by reference. For example, the nuclear, mitochondrial, and chloroplast genomes are functionally introduced into algae through a variety of known methods, including by microparticle bombardment, or using glass bead methods.

Genetically Engineered Algal Cells

In a further aspect, the invention relates to an algal cell that includes a polynucleotide sequence that is genetically engineered to express a higher level of botryococcene synthase than a corresponding wild type algal cell, wherein the cell produces an increased level of a botryococcene hydrocarbon molecule than a corresponding wild type algal cell.

The term "algal cell" refers to a eukaryotic cell containing one or multiple plastids. The term "algal cell" also includes cells belonging to the group of cyanophyta. Algae are unicellular or multicellular, photosynthetic, oxygenic, and are organisms without true roots, stems, or leaves. Algae contain chlorophyll and can vary in size from microscopic unicellular forms of smaller than 10 μm (microns) to large macroscopic multi-cellular forms up to dozens of meters long. The algal cell may be from green, blue-green, red, or brown algae. Preferably, the algal cell is a cell from green algae.

The algal cell may be derived from any macroalgae or microalgae organism. The algae can be unicellular or multi-cellular organisms. In some instances the organism is a rhodophyte, chlorophyte, heterokontophyte, tribophyte, glaucophyte, chlorarachniophyte, euglenoid, haptophyte, cryptomonad, dinoflagellum, or phytoplankton. Algae strains from which the algal cell may be derived include, for example, *Chlamydomonas reinhardtii*, *Volvox carteri*, *Chlorella* sp. NC64A, *Chlorella vulgaris*, *Ostreococcus tauri*, *Ostreococcus lucimarinus*, *Thalassiosira pseudonana*, *Pheodactylum tricornutum*, and *Aureococcus anophageferens*.

The algal cell may include a polynucleotide sequence that is genetically engineered by any method and means as described above to increase expression of a polynucleotide sequence that encodes the desired polypeptide sequence in the algal cell, when compared to a corresponding wild type algal cell.

A "wild type algal cell" refers to an algal cell that has not been genetically engineered or treated in an experimental sense or an algal cell that has the characteristics of an algal cell isolated from a naturally occurring source. A "corresponding" wild type algal cell refers to a wild type algal cell that is of the same species as the genetically engineered algal cell.

EXAMPLES

Example 1

The phytoene synthase protein sequence was of the green alga *Chlamydomonas reinhardtii* was obtained from the genome portal of the US DOE Joint Genome Institute located in Walnut Creek, Calif. This phytoene synthase protein sequence was initially used to perform a BLASTn search in other algal genomes, which are available through portals on the webpage of the Joint Genome Institute. The BLASTn search tool is integrated into the genome portal. BLASTn uses a protein sequence to search against translated nucleotide sequences. If possible genomic scaffolds were included in the BLASTn search. In addition, the partial sequence of the enzyme annotated so far as a phytoene/squalene synthase in the *Chlamydomonas reinhardtii* genome was used to identify similar sequences in other algal genomes. Further, the 'advanced search' search tool that is integrated to the genome portal of each genome was used to identify genes that were annotated and contain the terms 'phytoene' or 'squalene'. Protein sequences from all genes identified were then taken and aligned using the 'MegAlign' program from DNASTAR. In addition, all protein sequences from the protein dataset were multiply aligned using the program ClustalW, version 1.83 (Thompson et al. 1994). A primary PSY phylogenetic tree was constructed in MrBayes, version 3.12 (Huelsenbeck and Ronquist 2001), under 100,000 runs, using the Jones amino acid substitution matrix with a Wxed rate among sites. A second PSY phylogenetic tree was constructed using the Seqboot, Neighbor, and Consense programs in the Phylip package, version 3.66 (Felsenstein 1989). Bootstrap support values were derived from 100 randomized, replicate datasets. The resulting tree contains three major clades, one for the phytoene synthase, one for the squalene synthase, and a third clade for a related enzyme which was proposed to be a botryococcene synthase. Each protein sequence grouping into the third clade was then independently used to perform a BLAST search in the NCBI database of the NIH to veryfiy its annotation as a prenyltransferase.

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Apr. 26, 2011. The sequence listing.txt file is 37 kb in size.

What is claimed is:

1. A method for increasing the production level of a botryococcene hydrocarbon molecule in a cell, said method comprising functionally introducing at least one polynucleotide sequence comprising SEQ ID NO: 5 into said cell, wherein said polynucleotide sequence is under the control of an inducible promoter; and inducing expression of said polynucleotide sequence.

2. An algal cell comprising a vector, said vector comprises a nucleic acid molecule that encodes botryococcene synthase, wherein said botryococcene synthase comprises an amino acid sequence consisting of SEQ ID NO: 6.

3. The algal cell according to claim 2, wherein said amino acid sequence is at least 90% identical to SEQ ID NO: 6, and wherein the botryococcene synthase has a condensation activity.

4. A vector comprising a nucleic acid molecule that encodes a botryococcene synthase polypeptide, said polypeptide consisting of SEQ ID NO: 6.

5. The vector according to claim 4, wherein said vector comprises a polynucleotide of SEQ ID NO: 5.

6. The vector according to claim 4, wherein said vector comprises an enhancer.

7. The vector according to claim 4, wherein said vector comprises a promoter selected from the group of promoters consisting of constitutive promoters, inducible promoters, and viral promoters.

* * * * *

SEQUENCE LISTING

<160> NUMBER OF SEQ ID NOS: 18

<210> SEQ ID NO 1
<211> LENGTH: 585
<212> TYPE: DNA
<213> ORGANISM: Chlamydomonas reinhardtii

<400> SEQUENCE: 1
gagagcgtgg tggggcaaat ccgcttccag tggtggcgcg acgcggtgcg ggcggcctac      60
gaggaccggc cgcccaacca ccccgtggcc atcgccctgg cacacgtgct gcacagcccc     120
gggcccacgc cgccgcccgc cccggctcgc atcatcgacg tgcgtgaatc ggacttcctg     180

```
gacccgcagc cgccgctgga catgggcgcg ctggagagct acgcggaggg caccgcctcg    240
cagctgctgt acctgcagct ggcggctgcg ggcatcaagc accgcgacgc cgaccacgcc    300
gcctcgcacc tgggtcgggc cgtaggcatc accacgctgc tgcgcggcat gccggtgcac    360
gcggcggcgc ggcgcagcta cctgcccgtg gacctgtgcg cggaggcgcg cgtgtcgcag    420
gaggacgtgt acagcggcgt agtgagcgag gggctgcggg acgtggcgca caaggtggcc    480
agcctggcca agggccatct ggacgaggcc cgccgcctgg cgcctcggct gccccgggc     540 gcggcgggac tcatgctgcc tgccgtggcg gtggacaggt acctg                    585
```

<210> SEQ ID NO 2
<211> LENGTH: 195
<212> TYPE: PRT
<213> ORGANISM: Chlamydomonas reinhardtii

<400> SEQUENCE: 2

Glu Ser Val Val Gly Gln Ile Arg Phe Gln Trp Trp Arg Asp Ala Val
1               5                   10                  15

Arg Ala Ala Tyr Glu Asp Arg Pro Pro Asn His Pro Val Ala Ile Ala
                20                  25                  30

Leu Ala His Val Leu His Ser Pro Gly Pro Thr Pro Pro Ala Pro
            35                  40                  45

Ala Arg Ile Ile Asp Val Arg Glu Ser Asp Phe Leu Asp Pro Gln Pro
        50                  55                  60

Pro Leu Asp Met Gly Ala Leu Glu Ser Tyr Ala Glu Gly Thr Ala Ser
65                  70                  75                  80

Gln Leu Leu Tyr Leu Gln Leu Ala Ala Ala Gly Ile Lys His Arg Asp
                85                  90                  95

Ala Asp His Ala Ala Ser His Leu Gly Arg Ala Val Gly Ile Thr Thr
            100                 105                 110

Leu Leu Arg Gly Met Pro Val His Ala Ala Ala Arg Arg Ser Tyr Leu
        115                 120                 125

Pro Val Asp Leu Cys Ala Glu Ala Arg Val Ser Gln Glu Asp Val Tyr
    130                 135                 140

Ser Gly Val Val Ser Glu Gly Leu Arg Asp Val Ala His Lys Val Ala
145                 150                 155                 160

Ser Leu Ala Lys Gly His Leu Asp Glu Ala Arg Arg Leu Ala Pro Arg
                165                 170                 175

Leu Pro Pro Gly Ala Ala Gly Leu Met Leu Pro Ala Val Ala Val Asp
            180                 185                 190

Arg Tyr Leu
        195

<210> SEQ ID NO 3
<211> LENGTH: 903
<212> TYPE: DNA
<213> ORGANISM: Volvox carteri

<400> SEQUENCE: 3

```
atgatacatg gctctccag cgggctgccg aaggcacgcg ttctgtgggg tcactttgga     60
cagcagcggg cgagcaacgc cattgctcgc tcatatgcat ccttacctga ggacttgagg    120
tctgctttcg gcttctgtgt gcaacaggtc aggcagtatg actacctgaa ctacgtctgg    180
gtggcgcaga tgccaaagga tctgcggcct tcgctgttcg cgttgcgcgc cttcaacatc    240
gagacggctc tggtggcgga cagcgtccgc agcaaggagt cggtggtggg ccagatccgc    300
```

```
ttccagtggt ggcgagacgc ggtcaaagcc gccttcgaaa accggccgcc gaaccatccg    360
gtggcgtttg gaggcgctgc tggaaacagc ccgtcacgct tcagccgtta ctgctttaag    420
cgcatcattg actgccgtga ggcggatttc ttggacccac agccgccgct ggaccttcag    480
gcgctcgagc agtacgcgga gggaacgtcg tctcagctca tgtacttgca gctggcggct    540
gccggtgtga agcaccagga cgcggatcat gcagcatcgc acctaggtcg cgcagcgggt    600
atcaccacgc tcttgcgcgg cacagccgcc cacgccgcgg cacggcgctg ctacctgccc    660
gttgacttgt gcgcggaggc gcgcgtttcg caggaggatg tgtacagcgg cgtggtttcg    720
gagggactgc gtgatgtcgt acacaaagtc gccagcttgg ccaagggca tctggacgag    780 gcgcgacgac tggcgccgcg gctgccgcca ggcgctgctg gggtgatgct gccggcggtg    840
gcagtggggc gatacttgga ggggctggag gctgtgaact caacccata tgagacgaaa    900 ctc                                                                 903
```

<210> SEQ ID NO 4
<211> LENGTH: 301
<212> TYPE: PRT
<213> ORGANISM: Volvox carteri

<400> SEQUENCE: 4

```
Met Ile His Gly Leu Ser Ser Gly Leu Pro Lys Ala Arg Val Leu Trp
1               5                   10                  15

Gly His Phe Gly Gln Gln Arg Ala Ser Asn Ala Ile Ala Arg Ser Tyr
            20                  25                  30

Ala Ser Leu Pro Glu Asp Leu Arg Ser Ala Phe Gly Phe Cys Val Gln
        35                  40                  45

Gln Val Arg Gln Tyr Asp Tyr Leu Asn Tyr Val Trp Val Ala Gln Met
    50                  55                  60

Pro Lys Asp Leu Arg Pro Ser Leu Phe Ala Leu Arg Ala Phe Asn Ile
65                  70                  75                  80

Glu Thr Ala Leu Val Ala Asp Ser Val Arg Ser Lys Glu Ser Val Val
                85                  90                  95

Gly Gln Ile Arg Phe Gln Trp Trp Arg Asp Ala Val Lys Ala Ala Phe
            100                 105                 110

Glu Asn Arg Pro Pro Asn His Pro Val Ala Phe Gly Gly Ala Ala Gly
        115                 120                 125

Asn Ser Pro Ser Arg Phe Ser Arg Tyr Cys Phe Lys Arg Ile Ile Asp
    130                 135                 140

Cys Arg Glu Ala Asp Phe Leu Asp Pro Gln Pro Pro Leu Asp Leu Gln
145                 150                 155                 160

Ala Leu Glu Gln Tyr Ala Glu Gly Thr Ser Ser Gln Leu Met Tyr Leu
                165                 170                 175

Gln Leu Ala Ala Ala Gly Val Lys His Gln Asp Ala Asp His Ala Ala
            180                 185                 190

Ser His Leu Gly Arg Ala Ala Gly Ile Thr Thr Leu Leu Arg Gly Thr
        195                 200                 205

Ala Ala His Ala Ala Ala Arg Arg Cys Tyr Leu Pro Val Asp Leu Cys
    210                 215                 220

Ala Glu Ala Arg Val Ser Gln Glu Asp Val Tyr Ser Gly Val Val Ser
225                 230                 235                 240

Glu Gly Leu Arg Asp Val Val His Lys Val Ala Ser Leu Ala Lys Gly
                245                 250                 255
```

```
His Leu Asp Glu Ala Arg Arg Leu Ala Pro Arg Leu Pro Pro Gly Ala
            260                 265                 270

Ala Gly Val Met Leu Pro Ala Val Ala Val Gly Arg Tyr Leu Glu Gly
        275                 280                 285

Leu Glu Ala Val Asn Phe Asn Pro Tyr Glu Thr Lys Leu
        290                 295                 300

<210> SEQ ID NO 5
<211> LENGTH: 1143
<212> TYPE: DNA
<213> ORGANISM: Chlorella sp. NC64A

<400> SEQUENCE: 5
atgctggccc ggcgctgcct ggcagccacc gcaaacggca gccagcattt gcagtgtgca      60
gcagggctgt cccaattgag cagcagcgcc tatggcgttg ccggcggcgg cgccgcttct     120
gccgccgtgg gcggcggccg ctgctacgcc ggcagcgctg ggagtggcgg cgaggcaccg     180
gccgacatcc gcaaggcctt tgcctactgc gtggagcagg tgaagaagca cgactacgaa     240
aactacctct gggtcaccca gctgcccaag cccctgaggg ctcccatctt tgcgctgcgg     300
gcgttcaacg tggagacagg cctgatcagc cagcaagcca gtcggagat gctggtgctc      360 atgcggtgcc agcagtggtg gcgcgacgcg gtgaacgact gcttcaaggg gcggccccg      420 gagcagccgg tggtgacggc gctggcagag gtgctgcgcg tggtaccgct gacgcggtac     480
cgcctgcagc agatggtgag cacacgagag gaggacctgc tggcccacgc gcagcctgcc     540
agcctggagg cggtggagcg gtacgcagag ggcacctcgg gccagctgct gctgctgcag     600
ctggaggctg cacgcatcgg cgcaggcagc gctggcgctg gaggcggcag cagcagcgac     660
gacggcagcg gcagcacgcc tagtagcggc agcagccctg caggaggagg aggcggagcg     720
gcggcggcgg cggagcatgg ggcggcgcac ctgggcaagg cggtgggcat tgtgggcctg     780
ctgcgcggca cgtatgcgct gggcagccag cggcgggtat acctccccgc cgacctgtgc     840
cagcggcacg gcgtggggga tgaggacgtg ctggctgggc gcgactcgcc agggctgcgc     900
gacgtgacgc tggccgtcgc ctccgccgcc aagcagcacc tggacgacgc gcggcggctg     960
gcggctgacg tggcgccagc cgcgcggccc ctctttgcgc ccgccgtggc ggccgccatg    1020
tacttgcagg cgctggagca ggcgggcttc aacctgttcg accagcgcat gctgcggggg    1080
gccttctccc cgctggccta ccagctgcgc ctcaagtggg cgctgctgcg caacagctac    1140
tga                                                                  1143

<210> SEQ ID NO 6
<211> LENGTH: 380
<212> TYPE: PRT
<213> ORGANISM: Chlorella sp. NC64A

<400> SEQUENCE: 6

Met Leu Ala Arg Arg Cys Leu Ala Ala Thr Ala Asn Gly Ser Gln His
1               5                   10                  15

Leu Gln Cys Ala Ala Gly Leu Ser Gln Leu Ser Ser Ser Ala Tyr Gly
            20                  25                  30

Val Ala Gly Gly Gly Ala Ala Ser Ala Ala Val Gly Gly Gly Arg Cys
        35                  40                  45

Tyr Ala Gly Ser Ala Gly Ser Gly Gly Glu Ala Pro Ala Asp Ile Arg
    50                  55                  60

Lys Ala Phe Ala Tyr Cys Val Glu Gln Val Lys Lys His Asp Tyr Glu
65                  70                  75                  80
```

```
Asn Tyr Leu Trp Val Thr Gln Leu Pro Lys Pro Leu Arg Ala Pro Ile
                 85                  90                  95

Phe Ala Leu Arg Ala Phe Asn Val Glu Thr Gly Leu Ile Ser Gln Gln
            100                 105                 110

Ala Lys Ser Glu Met Leu Val Leu Met Arg Cys Gln Gln Trp Trp Arg
            115                 120                 125

Asp Ala Val Asn Asp Cys Phe Lys Gly Arg Pro Pro Glu Gln Pro Val
            130                 135                 140

Val Thr Ala Leu Ala Glu Val Leu Arg Val Val Pro Leu Thr Arg Tyr
145                 150                 155                 160

Arg Leu Gln Gln Met Val Ser Thr Arg Glu Glu Asp Leu Leu Ala His
                165                 170                 175

Ala Gln Pro Ala Ser Leu Glu Ala Val Glu Arg Tyr Ala Glu Gly Thr
            180                 185                 190

Ser Gly Gln Leu Leu Leu Leu Gln Leu Glu Ala Ala Arg Ile Gly Ala
            195                 200                 205

Gly Ser Ala Gly Ala Gly Gly Ser Ser Ser Asp Asp Gly Ser Gly
210                 215                 220

Ser Thr Pro Ser Ser Gly Ser Ser Pro Ala Gly Gly Gly Gly Ala
225                 230                 235                 240

Ala Ala Ala Glu His Gly Ala Ala His Leu Gly Lys Ala Val Gly
                245                 250                 255

Ile Val Gly Leu Leu Arg Gly Thr Tyr Ala Leu Gly Ser Gln Arg Arg
                260                 265                 270

Val Tyr Leu Pro Ala Asp Leu Cys Gln Arg His Gly Val Gly Asp Glu
            275                 280                 285

Asp Val Leu Ala Gly Arg Asp Ser Pro Gly Leu Arg Asp Val Thr Leu
            290                 295                 300

Ala Val Ala Ser Ala Ala Lys Gln His Leu Asp Asp Ala Arg Arg Leu
305                 310                 315                 320

Ala Ala Asp Val Ala Pro Ala Ala Arg Pro Leu Phe Ala Pro Ala Val
            325                 330                 335

Ala Ala Ala Met Tyr Leu Gln Ala Leu Glu Gln Ala Gly Phe Asn Leu
            340                 345                 350

Phe Asp Gln Arg Met Leu Arg Gly Ala Phe Ser Pro Leu Ala Tyr Gln
            355                 360                 365

Leu Arg Leu Lys Trp Ala Leu Leu Arg Asn Ser Tyr
        370                 375                 380

<210> SEQ ID NO 7
<211> LENGTH: 870
<212> TYPE: DNA
<213> ORGANISM: Chlorella vulgaris

<400> SEQUENCE: 7
atggcccagc aaaatctgcg atctgctctg gcgtattgtg tgaaccaagt cagatccttt      60
gactacacaa actacgtctg gaccattcag atgccaaagg agctgcgagc cgctgctgata    120 gcgctgcgag ccttcaatgt ggagctgacg cagatccctg acaacgtgaa gcaggagcag    180
ctgatgcaga ttcgcatgca gtggtggcgg gacgccgtca agagcgccta cacagacaag    240
ccgcagccca atccagtcat ccaggccctg cacgcggcgg tggcgtcggt gccgcggacg    300
cagtcgcacc tgttgcgcat ggtgagcacc ctggaggcgg actacatgcg cgcgcagccg    360
ccccaatcac tggagcagct ggagcagtat gcagagggca gctcctccca gctgctctac    420
```

```
ctccagggca gggttgcagg ggtggatgat gagcactttg accacgccgc ctcccacctc      480
ggcaaagctg tggggatcgc caaccttttg cggggaccg cctaccatgc tgccaggagg       540
cggtgctacc tgccgagcga cctgtgcatg agtgagggag tctcagatga agatgtgctg      600
cggggccaga acaccgacaa tgtctccaac gttgttttcc aagtagccac ccaggccaag      660
ggccatttgg acgaggcaag ggcgcttagc aagcagttac cggcagaggc aaagccgcta      720
atgctgccag ctcggcagt ggatttgtat ctgaaggccc tggagaagca cgagttcaat      780
gcctttgcgc cgcagctgca gtccggcggg ttcacacccc tctggcacca gcttctggtc      840
aagtacaacc tgatgcttgg cagattttga                                       870
```

```
<210> SEQ ID NO 8
<211> LENGTH: 289
<212> TYPE: PRT
<213> ORGANISM: Chlorella vulgaris

<400> SEQUENCE: 8

Met Ala Gln Gln Asn Leu Arg Ser Ala Leu Ala Tyr Cys Val Asn Gln
1               5                   10                  15

Val Arg Ser Phe Asp Tyr Thr Asn Tyr Val Trp Thr Ile Gln Met Pro
            20                  25                  30

Lys Glu Leu Arg Ala Pro Leu Ile Ala Leu Arg Ala Phe Asn Val Glu
        35                  40                  45

Leu Thr Gln Ile Pro Asp Asn Val Lys Gln Glu Gln Leu Met Gln Ile
    50                  55                  60

Arg Met Gln Trp Trp Arg Asp Ala Val Lys Ser Ala Tyr Thr Asp Lys
65                  70                  75                  80

Pro Gln Pro Asn Pro Val Ile Gln Ala Leu His Ala Ala Val Ala Ser
                85                  90                  95

Val Pro Arg Thr Gln Ser His Leu Leu Arg Met Val Ser Thr Leu Glu
            100                 105                 110

Ala Asp Tyr Met Arg Ala Gln Pro Pro Gln Ser Leu Glu Gln Leu Glu
        115                 120                 125

Gln Tyr Ala Glu Gly Ser Ser Ser Gln Leu Leu Tyr Leu Gln Gly Arg
    130                 135                 140

Val Ala Gly Val Asp Asp Glu His Phe Asp His Ala Ala Ser His Leu
145                 150                 155                 160

Gly Lys Ala Val Gly Ile Ala Asn Leu Leu Arg Gly Thr Ala Tyr His
                165                 170                 175

Ala Ala Arg Arg Arg Cys Tyr Leu Pro Ser Asp Leu Cys Met Ser Glu
            180                 185                 190

Gly Val Ser Asp Glu Asp Val Leu Arg Gly Gln Asn Thr Asp Asn Val
        195                 200                 205

Ser Asn Val Val Phe Gln Val Ala Thr Gln Ala Lys Gly His Leu Asp
    210                 215                 220

Glu Ala Arg Ala Leu Ser Lys Gln Leu Pro Ala Glu Ala Lys Pro Leu
225                 230                 235                 240

Met Leu Pro Ala Ala Val Asp Leu Tyr Leu Lys Ala Leu Glu Lys
                245                 250                 255

His Glu Phe Asn Ala Phe Ala Pro Gln Leu Gln Ser Gly Gly Phe Thr
            260                 265                 270

Pro Leu Trp His Gln Leu Leu Val Lys Tyr Asn Leu Met Leu Gly Arg
        275                 280                 285

Phe
```

```
<210> SEQ ID NO 9
<211> LENGTH: 453
<212> TYPE: DNA
<213> ORGANISM: Ostreococcus tauri

<400> SEQUENCE: 9
atgacgctcg cgttggacgc gtgcgggatc aggaacacgg acgcggatca cgcggccagt     60
catctcggga aggcgattgg attgagtgca ttactgcgcg ggacgacggc gcactcgcgt    120
cagaggcgat gttaccttcc gattgacgtc tgcgcgcgcc acggcgtgag cacgagagc    180 gtctatcgca tggaaccgag cgagggcgtg cgaagcgcgg cgcacgaggt ggcgtgcgcg    240
gcgaaggcgc acttagacag cgctcgcgcg atgacggaac gagttccgaa ggaggccaag    300
ccgttcttct acaagcggt gacggttgga cggtacctag acgcgctcga ggcgcgagac    360
tttgacgtct cgacgaaac cgtcgccaag ggcggcgcgc cgctcgcgac tcagggcgcg    420
atcgcgtggc atgcgtttcg agggacgtat tag                                453

<210> SEQ ID NO 10
<211> LENGTH: 150
<212> TYPE: PRT
<213> ORGANISM: Ostreococcus tauri

<400> SEQUENCE: 10

Met Thr Leu Ala Leu Asp Ala Cys Gly Ile Arg Asn Thr Asp Ala Asp
1               5                   10                  15

His Ala Ala Ser His Leu Gly Lys Ala Ile Gly Leu Ser Ala Leu Leu
            20                  25                  30

Arg Gly Thr Thr Ala His Ser Arg Gln Arg Arg Cys Tyr Leu Pro Ile
        35                  40                  45

Asp Val Cys Ala Arg His Gly Val Ser Thr Glu Ser Val Tyr Arg Met
    50                  55                  60

Glu Pro Ser Glu Gly Val Arg Ser Ala Ala His Glu Val Ala Cys Ala
65                  70                  75                  80

Ala Lys Ala His Leu Asp Ser Ala Arg Ala Met Thr Glu Arg Val Pro
                85                  90                  95

Lys Glu Ala Lys Pro Phe Phe Leu Gln Ala Val Thr Val Gly Arg Tyr
            100                 105                 110

Leu Asp Ala Leu Glu Ala Arg Asp Phe Asp Val Phe Asp Glu Thr Val
        115                 120                 125

Ala Lys Gly Gly Ala Pro Leu Ala Thr Gln Gly Ala Ile Ala Trp His
    130                 135                 140

Ala Phe Arg Gly Thr Tyr
145                 150

<210> SEQ ID NO 11
<211> LENGTH: 879
<212> TYPE: DNA
<213> ORGANISM: Ostreococcus lucimarinus

<400> SEQUENCE: 11
tcgacgagcg cgtccacgga cgatctgcgc gccgcgtttc gtcactgcgt cgaaatcgtt     60
cgcgcgagag actacgaaac ctatctctgc acgctcgccc tgccccgcgc gagcgcgccc    120
gcggcgttcg ccgtgcgcgc gctgaacgcg gagaccggtt cggtggtcgg aacgcggaa    180 tccgtcgacg cggcggtggc gcggttgatg tggtggcgag agacgatgac ggcggggagc    240
gccgggacac gggcgggtca cccggtggcg ctcgcaacgc tcgcagcgct gggaaacgag    300
```

```
ccgaacgcgc gcgcgagaac ttggatgcga cgaatgattg aggcgaggat cgcggacgcg      360
cgctcggatg daccgccgcg gacgattgca gatctagagc ggtatgcgag cgacgcgcac      420
gggagcgcgt tgacgctcgc gctcgacgcg tgcggagtca ggaatgcgga cgcggatcac      480
gcggtgagtc acttagggca agcgatagga ctaagtgcgt tattgcgcgg taccgtggcg      540
cacgcgaaac agcgtcgatg ttacttaccg agcgacgcgt gcgcgcggca cggggtgagc      600
accgagagcg tctatcgcat ggagccgagc gagggcgtgc gtaacgtcgc gcacgaagtc      660
gcgagcgcgg ccaaggggca tttagatagc gcgcgcgcga tggcgagcag agttcccgac      720
gacgccaagc cgttccttct gcaagcggtc cccgttggga ggtatttaga cgcgctcgag      780
gcgagagatt tcgacgtttt cgacgaagcc gtcgccaagg gcggcgcccc gctcttgacg      840
caaggcgcca tcgcctggca cgcgttcaaa cgcgcgtat                             879

<210> SEQ ID NO 12
<211> LENGTH: 293
<212> TYPE: PRT
<213> ORGANISM: Ostreococcus lucimarinus

<400> SEQUENCE: 12

Ser Thr Ser Ala Ser Thr Asp Asp Leu Arg Ala Ala Phe Arg His Cys
1               5                   10                  15

Val Glu Ile Val Arg Ala Arg Asp Tyr Glu Thr Tyr Leu Cys Thr Leu
            20                  25                  30

Ala Leu Pro Arg Ala Ser Ala Pro Ala Ala Phe Ala Val Arg Ala Leu
        35                  40                  45

Asn Ala Glu Thr Gly Ser Val Val Gly Asn Ala Glu Ser Val Asp Ala
    50                  55                  60

Ala Val Ala Arg Leu Met Trp Trp Arg Glu Thr Met Thr Ala Gly Ser
65                  70                  75                  80

Ala Gly Thr Arg Ala Gly His Pro Val Ala Leu Ala Thr Leu Ala Ala
                85                  90                  95

Leu Gly Asn Glu Pro Asn Ala Arg Ala Arg Thr Trp Met Arg Arg Met
            100                 105                 110

Ile Glu Ala Arg Ile Ala Asp Ala Arg Ser Asp Gly Pro Pro Arg Thr
        115                 120                 125

Ile Ala Asp Leu Glu Arg Tyr Ala Ser Asp Ala His Gly Ser Ala Leu
    130                 135                 140

Thr Leu Ala Leu Asp Ala Cys Gly Val Arg Asn Ala Asp Ala Asp His
145                 150                 155                 160

Ala Val Ser His Leu Gly Gln Ala Ile Gly Leu Ser Ala Leu Leu Arg
                165                 170                 175

Gly Thr Val Ala His Ala Lys Gln Arg Arg Cys Tyr Leu Pro Ser Asp
            180                 185                 190

Ala Cys Ala Arg His Gly Val Ser Thr Glu Ser Val Tyr Arg Met Glu
        195                 200                 205

Pro Ser Glu Gly Val Arg Asn Val Ala His Glu Val Ala Ser Ala Ala
    210                 215                 220

Lys Gly His Leu Asp Ser Ala Arg Ala Met Ala Ser Arg Val Pro Asp
225                 230                 235                 240

Asp Ala Lys Pro Phe Leu Leu Gln Ala Val Pro Val Gly Arg Tyr Leu
                245                 250                 255

Asp Ala Leu Glu Ala Arg Asp Phe Asp Val Phe Asp Glu Ala Val Ala
            260                 265                 270
```

Lys Gly Gly Ala Pro Leu Leu Thr Gln Gly Ala Ile Ala Trp His Ala
            275                 280                 285

Phe Lys Arg Ala Tyr
        290

<210> SEQ ID NO 13
<211> LENGTH: 987
<212> TYPE: DNA
<213> ORGANISM: Thalassiosira pseudonana

<400> SEQUENCE: 13

```
atgccttcct ctgcaagaga agcattcttt gcactacgag ctttcaatgt tgaaattgcg      60
agtatcaaag attcatctat gttaatgggt ggaagatctc gtggacgtcg tgacactgat     120
ggggaaggag aggggatggg tgactcctcg ctggcttcta gattacgaat gcagtggtgg     180
cgcgatggta tagcggaagt gtacgacgat atggatacta cggatgacct acaacagaaa     240
caatcatcac aagatccaat ccttcgttca ttgacctctt cacgaaagct caatccaacg     300
ttgcggagtc tgacacaagc gattcatact catcaattga cgcatcggtt tctgaggaga     360
atgatggaag caagagaaaa agatttagag gtgatgcagt atgagaggta tagggatgtc     420
gctcagtacg gggaggatac tgtttcgagt gtgttgtatt tgagtttgga gtgtgttggg     480
gttcgagacg atcaatcgga tttagtggcc tcggacatcg tgttggtct  aggactcatc     540
acttcgctca gatctaccgc gtttcgtgct actcaaggag aatgctccgt tccttttgat     600
cttgcaacta acactctgt  tacaatggat accatttgga gtgcttggaa tgcatcaaat     660
aacgatattg ttactgagaa cgaagaatca aagtcggctc aggaagcatt acgggataca     720
acacgtgaat tggcggcgat ggcagcgttt cacttgcatc gtgcacgcga aaatcaaggc     780
acggtgccga agaaggacg  gccgtgtctg ctgccagcag tatgcgggtt gcagtatctg     840
aatgcactgg aagcatgcaa ctttgatgtg ttgcatccat ctttagtggg cagttcagaa     900
ggcgatggtg acgtgggagt cgacagaagc agacgtttaa acttgatgct tcttcttggg     960
agagcctggt tgactggcac cttttga                                         987
```

<210> SEQ ID NO 14
<211> LENGTH: 328
<212> TYPE: PRT
<213> ORGANISM: Thalassiosira pseudonana

<400> SEQUENCE: 14

Met Pro Ser Ser Ala Arg Glu Ala Phe Phe Ala Leu Arg Ala Phe Asn
1               5                   10                  15

Val Glu Ile Ala Ser Ile Lys Asp Ser Ser Met Leu Met Gly Gly Arg
            20                  25                  30

Ser Arg Gly Arg Arg Asp Thr Asp Gly Glu Gly Glu Met Gly Asp
        35                  40                  45

Ser Ser Leu Ala Ser Arg Leu Arg Met Gln Trp Trp Arg Asp Gly Ile
    50                  55                  60

Ala Glu Val Tyr Asp Asp Met Asp Thr Thr Asp Asp Leu Gln Gln Lys
65                  70                  75                  80

Gln Ser Ser Gln Asp Pro Ile Leu Arg Ser Leu Thr Ser Ser Arg Lys
                85                  90                  95

Leu Asn Pro Thr Leu Arg Ser Leu Thr Gln Ala Ile His Thr His Gln
            100                 105                 110

Leu Thr His Arg Phe Leu Arg Arg Met Met Glu Ala Arg Glu Lys Asp
        115                 120                 125

```
Leu Glu Val Met Gln Tyr Glu Arg Tyr Arg Asp Val Ala Gln Tyr Gly
        130                 135                 140

Glu Asp Thr Val Ser Ser Val Leu Tyr Leu Ser Leu Glu Cys Val Gly
145                 150                 155                 160

Val Arg Asp Asp Gln Ser Asp Leu Val Ala Ser Asp Ile Gly Val Gly
                165                 170                 175

Leu Gly Leu Ile Thr Ser Leu Arg Ser Thr Ala Phe Arg Ala Thr Gln
                180                 185                 190

Gly Glu Cys Ser Val Pro Phe Asp Leu Ala Thr Lys His Ser Val Thr
                195                 200                 205

Met Asp Thr Ile Trp Ser Ala Trp Asn Ala Ser Asn Asn Asp Ile Val
        210                 215                 220

Thr Glu Asn Glu Glu Ser Lys Ser Ala Gln Glu Ala Leu Arg Asp Thr
225                 230                 235                 240

Thr Arg Glu Leu Ala Ala Met Ala Ala Phe His Leu His Arg Ala Arg
                245                 250                 255

Glu Asn Gln Gly Thr Val Pro Lys Glu Gly Arg Pro Cys Leu Leu Pro
                260                 265                 270

Ala Val Cys Gly Leu Gln Tyr Leu Asn Ala Leu Glu Ala Cys Asn Phe
                275                 280                 285

Asp Val Leu His Pro Ser Leu Val Gly Ser Ser Glu Gly Asp Gly Asp
        290                 295                 300

Val Gly Val Asp Arg Ser Arg Arg Leu Asn Leu Met Leu Leu Leu Gly
305                 310                 315                 320

Arg Ala Trp Leu Thr Gly Thr Phe
                325

<210> SEQ ID NO 15
<211> LENGTH: 2136
<212> TYPE: DNA
<213> ORGANISM: Pheodactylum tricornutum

<400> SEQUENCE: 15
atggggcgaa agaagaaaat tgcatcccag caaccggaat catcgaatca accggctaag      60
aaagcaaagc cagaaactgg tccgtcgttt ctcgtgaaaa agtaccggcc ggataagcat     120
tatgcatcga tggacgcttt cgtcaagtac gcgaagtctc accgaatgct ggacgcggcc     180
tatgtacaat ggacaaaagg cgtaacggcc gagaagccgt ttgttttttc tgtacgggtg     240 ggtgggtag acctcggttg ggggcggggg aagacgcgtg aggctgccat ggaatgtgcc      300
tgccgagcag cctttgcctt ggttggagct cacgggtata aaaattggac aattgatgac     360
aactgcttga tggaagaacc agtagatgtg cctcctccac caccgcctcc gatgcccggc     420
gcgatggcgc tcggcttgcc tccttaccct ccaggcagcc tccctcctcc tcccatgccc     480 ggcttttttac caccgcctcc ccttcccggt atgcttgcgc ctccgctgcc tcccggtgcg     540
ccaccgcttc ctgatgcacc cccacctcca atggcagcgg accttatccc tcagccccaa     600
atggtatcga accaagcgcc cgtagcaacg agcgtagcgt ccggtgtcgc caataatgtg     660
aactctgctg taagtgatgc gtatacaact tctgcaagcg tatctctcaa ttttggaaag     720
cctgctgttg tgaagagtca gcgaaagcaa ctcaagggtg gattgactct tgtgtacgat     780
ccgctctcgg aaggaatgga agaactgagt atggaagaac gacgagctag cctagaaaga     840
tatcaaaaaa tgttggtgcg ctctgtggcc aaggtggcga atagcggaga atttttttg      900 ggaatatcaa gaaacgtaag ttgttacatt ggcaatcttt ttggtgtctt gccggtaaag     960
```

```
cccatcattg gaagcattga ctatgaggta ataagaactt ttctcatggc ttcacttcta    1020
ctttcgctat tgacagtgag cagacgagcg agctctatga gtgtggctaa aggcgcattg    1080
actcgtcaag ggcctggcat ttatctatcg aagtcggcgc caattcgatg cacgcttcaa    1140
caacaacaac aacaatctct atcaaccaga agcagcgatg atcaacgaaa tcagagcgct    1200
ggtcaagtta tcaaggacca ccaatactgc gttgatcttg tccgcgagcg ggacagggaa    1260
ggataccgag ctaccaaagc gtactttgcc atacgggcct ttaatgttga gctagcgtcc    1320
gtcaaagact ctcacaactt cgccgtcgg gagcagcctg ccaacaaga gtcttcgagt     1380 agtgttgccc tgcaaatgcg catgcaatgg tggagagacg ccttgaagga aatttacgaa    1440
gacgaaatga gtgttgctgc tgatcctatt ctaaggaatc tatcggtgtc ctgctggcac    1500
aatcctgtcg ttcgagcttt gtcccaagct caccagcaat gtgacttgac acggcgcttc    1560
ctcgaacgct tgattgatgc tcgcgattac gacctcagtg ttgcgcagta ttcttcgatg    1620
aatgaagcgg caacctatgc agaggatacc atttcgagtc ttctgtacct agccctggag    1680
tgtacaggga ctcgcgacga caatgctgat gaagtcgctt catacgctgg tgtcgggata    1740
ggtctaacga cagccctacg cgcgacgccc tttcgattaa tgcatggtga aatacccatt    1800
ccaaaggatc tgctgcgccc agcttttcct taccaggaat tgatgaaaca gaccgaagag    1860
gaatatacgt tgatagaatc cgacgcgata gcatttcgcg aggcagtccg gcacatggca    1920
aatgctgctt ccaccagttt agctcgtgcg cgcgatattc aggggcatgt accgaggcat    1980
gctagagctt gcttgctacc ggttgtcccg tcaattcatt tccttttcaaa gctggagggc    2040 gtcgattatc acttgtttga cccgaagctg aacgatgaca cacgactgcg attaatgtta    2100
ctcatgggac gaacatggct cacaggaatc ttctag                              2136
```

<210> SEQ ID NO 16
<211> LENGTH: 711
<212> TYPE: PRT
<213> ORGANISM: Pheodactylum tricornutum

<400> SEQUENCE: 16

```
Met Gly Arg Lys Lys Ile Ala Ser Gln Gln Pro Glu Ser Ser Asn
1               5                   10                  15

Gln Pro Ala Lys Lys Ala Lys Pro Glu Thr Gly Pro Ser Phe Leu Val
                20                  25                  30

Lys Lys Tyr Arg Pro Asp Lys His Tyr Ala Ser Met Asp Ala Phe Val
            35                  40                  45

Lys Tyr Ala Lys Ser His Arg Met Leu Asp Ala Ala Tyr Val Gln Trp
        50                  55                  60

Asn Lys Gly Val Thr Ala Glu Lys Pro Phe Val Phe Ser Val Arg Val
65                  70                  75                  80

Gly Gly Val Asp Leu Gly Trp Gly Arg Gly Lys Thr Arg Glu Ala Ala
                85                  90                  95

Met Glu Cys Ala Cys Arg Ala Ala Phe Ala Leu Val Gly Ala His Gly
            100                 105                 110

Tyr Lys Asn Trp Thr Ile Asp Asp Asn Cys Leu Met Glu Glu Pro Val
        115                 120                 125

Asp Val Pro Pro Pro Pro Pro Pro Met Pro Gly Ala Met Ala Leu
    130                 135                 140

Gly Leu Pro Pro Tyr Pro Pro Gly Ser Leu Pro Pro Pro Met Pro
145                 150                 155                 160
```

```
Gly Phe Leu Pro Pro Pro Leu Pro Gly Met Leu Ala Pro Pro Leu
                165                 170                 175

Pro Pro Gly Ala Pro Pro Leu Pro Asp Ala Pro Pro Pro Met Ala
            180                 185                 190

Ala Asp Leu Ile Pro Gln Pro Gln Met Val Ser Asn Gln Ala Pro Val
        195                 200                 205

Ala Thr Ser Val Ala Ser Gly Val Ala Asn Asn Val Asn Ser Ala Val
    210                 215                 220

Ser Asp Ala Tyr Thr Thr Ser Ala Ser Val Leu Asn Phe Gly Lys
225                 230                 235                 240

Pro Ala Val Val Lys Ser Gln Arg Lys Gln Leu Lys Gly Gly Leu Thr
                245                 250                 255

Leu Val Tyr Asp Pro Leu Ser Glu Gly Met Glu Glu Leu Ser Met Glu
                260                 265                 270

Glu Arg Arg Ala Ser Leu Glu Arg Tyr Gln Lys Met Leu Val Arg Ser
            275                 280                 285

Val Ala Lys Val Ala Asn Ser Gly Glu Phe Phe Leu Gly Ile Ser Arg
    290                 295                 300

Asn Val Ser Cys Tyr Ile Gly Asn Leu Phe Gly Val Leu Pro Val Lys
305                 310                 315                 320

Pro Ile Ile Gly Ser Ile Asp Tyr Glu Val Ile Arg Thr Phe Leu Met
                325                 330                 335

Ala Ser Leu Leu Leu Ser Leu Leu Thr Val Ser Arg Arg Ala Ser Ser
            340                 345                 350

Met Ser Val Ala Lys Gly Ala Leu Thr Arg Gln Gly Pro Gly Ile Tyr
    355                 360                 365

Leu Ser Lys Ser Ala Pro Ile Arg Cys Thr Leu Gln Gln Gln Gln
370                 375                 380

Gln Ser Leu Ser Thr Arg Ser Ser Asp Gln Arg Asn Gln Ser Ala
385                 390                 395                 400

Gly Gln Val Ile Lys Asp His Gln Tyr Cys Val Asp Leu Val Arg Glu
            405                 410                 415

Arg Asp Arg Glu Gly Tyr Arg Ala Thr Lys Ala Tyr Phe Ala Ile Arg
    420                 425                 430

Ala Phe Asn Val Glu Leu Ala Ser Val Lys Asp Ser His Asn Leu Arg
435                 440                 445

Arg Arg Glu Gln Pro Gly Gln Gln Glu Ser Ser Ser Val Ala Leu
            450                 455                 460

Gln Met Arg Met Gln Trp Trp Arg Asp Ala Leu Lys Glu Ile Tyr Glu
465                 470                 475                 480

Asp Glu Met Ser Val Ala Ala Asp Pro Ile Leu Arg Asn Leu Ser Val
                485                 490                 495

Ser Cys Trp His Asn Pro Val Val Arg Ala Leu Ser Gln Ala His Gln
            500                 505                 510

Gln Cys Asp Leu Thr Arg Arg Phe Leu Glu Arg Leu Ile Asp Ala Arg
    515                 520                 525

Asp Tyr Asp Leu Ser Val Ala Gln Tyr Ser Ser Met Asn Glu Ala Ala
530                 535                 540

Thr Tyr Ala Glu Asp Thr Ile Ser Ser Leu Leu Tyr Leu Ala Leu Glu
545                 550                 555                 560

Cys Thr Gly Thr Arg Asp Asp Asn Ala Asp Glu Val Ala Ser Tyr Ala
                565                 570                 575
```

```
Gly Val Gly Ile Gly Leu Thr Thr Ala Leu Arg Ala Thr Pro Phe Arg
                580                 585                 590

Leu Met His Gly Glu Ile Pro Ile Pro Lys Asp Leu Leu Arg Pro Ala
            595                 600                 605

Phe Pro Tyr Gln Glu Leu Met Lys Gln Thr Glu Glu Glu Tyr Thr Leu
        610                 615                 620

Ile Glu Ser Asp Ala Ile Ala Phe Arg Glu Ala Val Arg His Met Ala
625                 630                 635                 640

Asn Ala Ala Ser Thr Ser Leu Ala Arg Ala Arg Asp Ile Gln Gly His
                645                 650                 655

Val Pro Arg His Ala Arg Ala Cys Leu Leu Pro Val Val Pro Ser Ile
            660                 665                 670

His Phe Leu Ser Lys Leu Glu Gly Val Asp Tyr His Leu Phe Asp Pro
        675                 680                 685

Lys Leu Asn Asp Asp Thr Arg Leu Arg Leu Met Leu Leu Met Gly Arg
        690                 695                 700

Thr Trp Leu Thr Gly Ile Phe
705                 710

<210> SEQ ID NO 17
<211> LENGTH: 687
<212> TYPE: DNA
<213> ORGANISM: Aureococcus anophagefferens

<400> SEQUENCE: 17
tccatctacg cctggtgccg gcgcgccgac gacgtcgccg acgaggtcgg cgtgaacaag      60
ggtttggcgc tcgcgagcct cgacgagatc gaggccgatc tggcggcggc gctccgcggg     120
agcccgcgga acgccatcga cgcggcgctc gccgcgacct cgaggcctac cccggcgctg     180
tcgacggcgc ccttcgaggc catgctcgag gcatgcgcg gcgacctgcg gccggagagt      240
ctacggttcg agcgctggga cccggacctg aaaacgtact gcgagcgcgt cgcgggcggc      300
gtggggctca tgctgctccc gctgctcggc gcgacacccg accccgtcgt ggagcggcgg     360
gccgtggacc tgggcgtcgc catccagctg acgaacgtgc tgagagatgt aggggcggac     420
gcgcgcgact acgaccgggt ctacctgccc ctggcggacc tcgcggcctg cggctgcgac     480
ctggaggacg tgcggaaggg gcggctgacg gcgccctaca aggacgccgt gcggctgcag     540
atatcgcgcg cgcgcgacct ctacgcgtcc gcgcgcctcg cgatcccgga cctgcccaag     600
gcgtcgcggc tgcccgtggc ggccatcgtc gagctgctcg agagcatcgt cgacgagctc     660
gaggcgcgcg actgcgactc gctctcg                                       687

<210> SEQ ID NO 18
<211> LENGTH: 229
<212> TYPE: PRT
<213> ORGANISM: Aureococcus anophagefferens

<400> SEQUENCE: 18

Ser Ile Tyr Ala Trp Cys Arg Arg Ala Asp Asp Val Ala Asp Glu Val
1               5                   10                  15

Gly Val Asn Lys Gly Leu Ala Leu Ala Ser Leu Asp Glu Ile Glu Ala
            20                  25                  30

Asp Leu Ala Ala Ala Leu Arg Gly Ser Pro Arg Asn Ala Ile Asp Ala
        35                  40                  45

Ala Leu Ala Ala Thr Phe Glu Ala Tyr Pro Ala Leu Ser Thr Ala Pro
    50                  55                  60
```

-continued

```
Phe Glu Ala Met Leu Glu Gly Met Arg Gly Asp Leu Arg Pro Glu Ser
 65                  70                  75                  80

Leu Arg Phe Glu Arg Trp Asp Pro Asp Leu Lys Thr Tyr Cys Glu Arg
             85                  90                  95

Val Ala Gly Gly Val Gly Leu Met Leu Leu Pro Leu Leu Gly Ala Thr
            100                 105                 110

Pro Asp Pro Val Val Glu Arg Arg Ala Val Asp Leu Gly Val Ala Ile
        115                 120                 125

Gln Leu Thr Asn Val Leu Arg Asp Val Gly Ala Asp Ala Arg Asp Tyr
        130                 135                 140

Asp Arg Val Tyr Leu Pro Leu Ala Asp Leu Ala Ala Cys Gly Cys Asp
145                 150                 155                 160

Leu Glu Asp Val Arg Lys Gly Arg Leu Thr Ala Pro Tyr Lys Asp Ala
                165                 170                 175

Val Arg Leu Gln Ile Ser Arg Ala Arg Asp Leu Tyr Ala Ser Ala Arg
            180                 185                 190

Leu Ala Ile Pro Asp Leu Pro Lys Ala Ser Arg Leu Pro Val Ala Ala
        195                 200                 205

Ile Val Glu Leu Leu Glu Ser Ile Val Asp Glu Leu Glu Ala Arg Asp
        210                 215                 220

Cys Asp Ser Leu Ser
225
```